(12) United States Patent
Swanson et al.

(10) Patent No.: US 12,090,475 B2
(45) Date of Patent: Sep. 17, 2024

(54) ANALYTICAL CARTRIDGE FOR SOIL TESTING AND RELATED METHODS

(71) Applicant: Precision Planting LLC, Tremont, IL (US)

(72) Inventors: Todd Swanson, Morton, IL (US); Dale Koch, Tremont, IL (US); Adam Vaccari, Tremont, IL (US)

(73) Assignee: Precision Planting LLC, Tremont, IL (US)

( * ) Notice: Subject to any disclaimer, the term of this patent is extended or adjusted under 35 U.S.C. 154(b) by 948 days.

(21) Appl. No.: 17/052,419

(22) PCT Filed: Apr. 11, 2019

(86) PCT No.: PCT/IB2019/052980
§ 371 (c)(1),
(2) Date: Nov. 2, 2020

(87) PCT Pub. No.: WO2019/211683
PCT Pub. Date: Nov. 7, 2019

(65) Prior Publication Data
US 2021/0053048 A1    Feb. 25, 2021

Related U.S. Application Data

(60) Provisional application No. 62/665,030, filed on May 1, 2018.

(51) Int. Cl.
*B01L 3/00* (2006.01)
*G01N 33/24* (2006.01)

(52) U.S. Cl.
CPC ............... *B01L 3/502* (2013.01); *B01L 3/52* (2013.01); *G01N 33/24* (2013.01);
(Continued)

(58) Field of Classification Search
CPC ....................................................... B01L 3/502
(Continued)

(56) References Cited

U.S. PATENT DOCUMENTS

2007/0125942 A1   6/2007   Kido
2013/0247655 A1   9/2013   Preiner et al.
(Continued)

FOREIGN PATENT DOCUMENTS

KR   2017 0048188 A   5/2017

OTHER PUBLICATIONS

European Patent Office, International Search Report for related International Application No. PCT/IB2019/052980, mail date Jul. 10, 2019.

*Primary Examiner* — Christine T Mui
*Assistant Examiner* — Emily R. Berkeley

(57) ABSTRACT

A rotary analysis apparatus and related methods are disclosed. The apparatus generally includes a rotary machine operable to rotate or spin a removable disk-type analytical cartridge. The cartridge includes a plurality of fluidly isolated processing trains for processing multiple samples simultaneously. Each process train includes an extractant mixing chamber, slurry filtration chamber, supernatant collection chamber, and reagent mixing chamber in fluid communication. In one use, soil sample slurry is prepared and added to the extractant mixing chamber. The slurry is mixed with an extractant by rotating the cartridge to separate out an analyte from the mixture. A sediment filter in the filtration chamber deliquifies and traps soil particles to produce clear supernatant. A color changing reagent or fluorescent agent may be mixed with the collected supernatant for subsequent colorimetric, fluorescent, turbidimetric, or other type of analysis.

23 Claims, 37 Drawing Sheets

(52) U.S. Cl.
CPC ... *B01L 2200/0631* (2013.01); *B01L 2200/10* (2013.01); *B01L 2200/16* (2013.01); *B01L 2300/04* (2013.01); *B01L 2300/0681* (2013.01); *B01L 2300/0803* (2013.01); *B01L 2300/0858* (2013.01); *B01L 2300/0864* (2013.01); *B01L 2400/0409* (2013.01); *G01N 33/245* (2024.05)

(58) Field of Classification Search
USPC .......................................................... 436/177
See application file for complete search history.

(56) References Cited

U.S. PATENT DOCUMENTS

| | | |
|---|---|---|
| 2015/0314290 A1 | 11/2015 | Cho et al. |
| 2015/0352545 A1 | 12/2015 | Taylor et al. |
| 2016/0018380 A1 | 1/2016 | Gerber-Siff et al. |
| 2016/0263577 A1 | 9/2016 | Ismagilov et al. |

ANALYTICAL CARTRIDGE FOR SOIL TESTING AND RELATED METHODS

CROSS-REFERENCE TO RELATED APPLICATIONS

The present application is a U.S. national stage application under 35 U.S.C. § 371 of PCT/IB2019/052980 filed Apr. 11, 2019, which claims of the benefit of priority to U.S. Provisional Application No. 62/665,030 filed May 1, 2018; the entireties of which are is incorporated herein by reference.

BACKGROUND

The present invention relates generally to analytical cartridges, and more particularly to a cartridge usable for performing fluid analysis, such as soil analysis, and related methods for use.

Soil testing is an important aspect of the agricultural arts. Test results provide valuable information on the chemical makeup and characteristics of the soil (e.g. levels of nitrogen, phosphorous, potassium, etc.) so that various amendments may be added to the soil to maximize the quality and quantity of crop production. Liquid cartridges have traditionally been used for soil testing in which a solid soil sample is added to the tube to which deionized water is added. After the static mixture rests for a period of time, the liquid is manually extracted from the sample and filtered for subsequent chemical analysis of the clear supernatant. This is generally a cumbersome process because the filtration process involves multiple sieving steps through progressively smaller size sieves in order to prevent blinding the finer sieves with smallest openings. In addition, samples are generally processed on a piece-meal basis for each analyte (i.e. substance or chemical constituent of interest) to be detected and analyzed.

Improvements in soil testing are desired.

BRIEF SUMMARY

The present invention provides an apparatus and related processes or methods for fluid analysis which allows multiple samples to be processed simultaneously and analyzed for different analytes and/or chemical properties without requiring multiple sieving steps. The analysis apparatus includes a rotary machine and removable disk-type analytical cartridge in one embodiment. The apparatus utilizes centrifugal force for automatically filtering and processing the samples. The disk cartridge comprises a plurality of different processing chambers for automatically mixing an extractant with a sample slurry to separate a particular analyte for analysis, filtering the slurry to yield a clear supernatant, and mixing a color changing reagent with the supernatant via rotary motion and centrifugal force.

The rotary machine operates to spin or rotate the cartridge in two different operating modes: a single rotational direction for multiple complete revolutions, or in a back and forth oscillating manner by repetitiously reversing direction rapidly in less than a full revolution. The former operating mode is advantageous for distributing the sample mixture through the various processing chambers by centrifugal force. The latter operating mode is beneficial for simply mixing the contents of a particular chamber. The present cartridge and process allows processing of multiple soil samples simultaneously in parallel for analysis, as further described herein. In one embodiment, colorimetric detection and analysis of the reagent infused supernatant samples using a colorimeter may be used. Colorimetric analysis utilizes reagents that changes color and intensity in the presence of an analyte. This allows the colorimeter to measure the concentration or amount of the analyte in the solution by measuring the absorbance of specific wavelengths of light associated with the substance. The colorimeter may be incorporated into the rotary machine in one embodiment.

In one aspect, an analytical cartridge for sample testing includes: a centerline axis; a main body defining a plurality of sample processing trains arranged around the centerline axis, the main body having a mounting opening configured for mounting to a spindle of a rotary machine; each processing train including an extractant mixing chamber having a slurry fill hole for introducing a soil slurry and an extractant, and a reagent mixing chamber fluidly coupled to the extractant mixing chamber. The cartridge may further include a sediment filter fluidly interposed between the extractant and reagent mixing chambers, the filter configured to deliquify the slurry for producing a supernatant collected in the reagent mixing chamber for analysis by removing dissolved and/or suspended particulate matter (including soil particles) from the slurry-extractant mixture.

In another aspect, a rotary soil analysis apparatus includes: a rotary machine comprising a rotating spindle; an analytical cartridge mounted on the spindle and rotatable with the spindle, the cartridge defining a plurality of fluidly isolated sample processing trains arranged around the centerline axis in sectors; each processing train including an extractant mixing chamber having a slurry fill hole for introducing a soil slurry and a reagent mixing chamber fluidly coupled to the extractant mixing chamber; and a sediment filter fluidly interposed between the extractant and reagent mixing chambers; wherein when the cartridge is spun by the rotary machine, the slurry flows from the extractant mixing chamber to the filter which deliquifies the slurry thereby producing a supernatant for analysis.

In another aspect, a method for analyzing a soil sample includes: providing a cartridge having at least one chamber; adding a soil slurry and a reagent to the cartridge; deliquifying the soil slurry to produce a supernatant; rotating the cartridge to mix the supernatant and the reagent into a supernatant-reagent mixture; and analyzing the supernatant-reagent mixture to measure a property of the soil.

BRIEF DESCRIPTION OF THE DRAWINGS

The present invention will become more fully understood from the detailed description and the accompanying drawings, wherein like elements are labeled similarly and in which.

Figure 1:
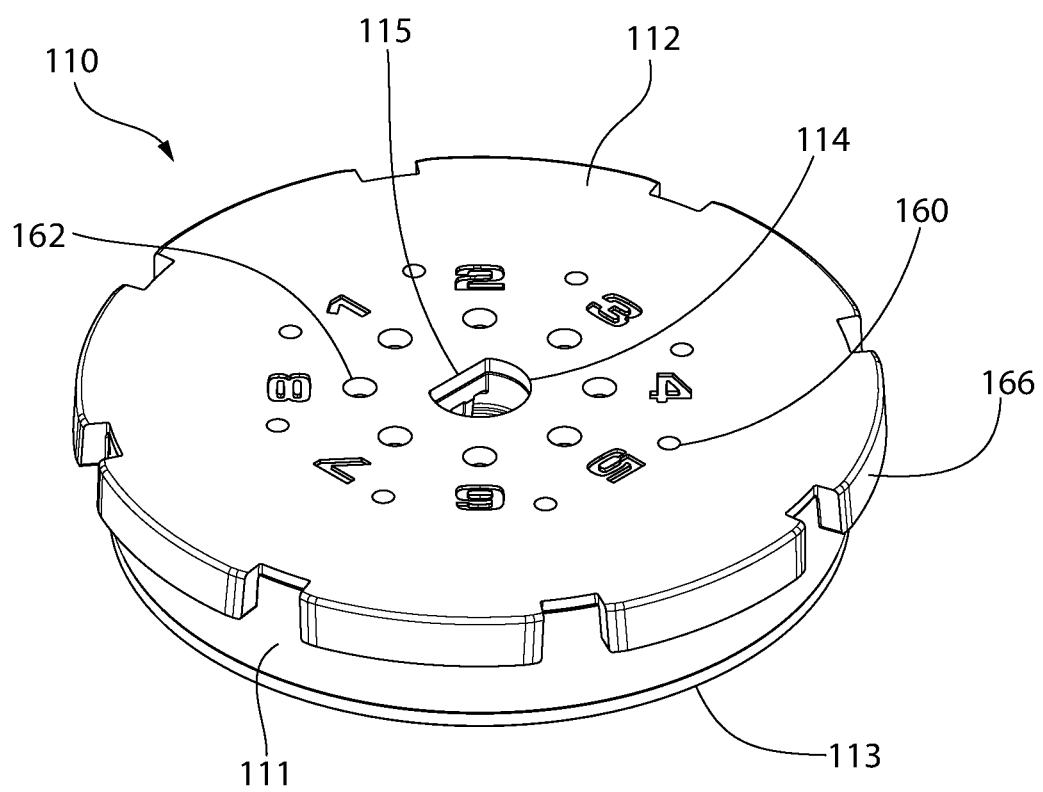
FIG. 1 is a top perspective view of a first analytical cartridge usable for soil testing according to the present disclosure.

All drawings are schematic and not necessarily to scale. Components numbered and appearing in one figure but appearing un-numbered in other figures are the same unless expressly noted otherwise. A reference herein to a whole figure number which appears in multiple figures bearing the same whole number but with different alphabetical suffixes shall be constructed as a general refer to all of those figures unless expressly noted otherwise.

DETAILED DESCRIPTION

The features and benefits of the invention are illustrated and described herein by reference to exemplary ("example") embodiments. This description of exemplary embodiments is intended to be read in connection with the accompanying drawings, which are to be considered part of the entire written description. Accordingly, the disclosure expressly should not be limited to such exemplary embodiments illustrating some possible non-limiting combination of features that may exist alone or in other combinations of features.

In the description of embodiments disclosed herein, any reference to direction or orientation is merely intended for convenience of description and is not intended in any way to limit the scope of the present invention. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise.

As used throughout, any ranges disclosed herein are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

The apparatus 100 described herein can test any type of fluid. In the embodiments described below, apparatus 100 is illustrated for soil analysis. FIGS. 1-17 and 34 illustrate a non-limiting example of a rotary soil analysis apparatus 100 according to the present disclosure. Apparatus 100 generally includes a rotary machine 101 which is shown with a first embodiment of removable disk-type rotary analytical cartridge 110 according to the present disclosure. Rotary machine 101 in one embodiment may include a stepped cylinder housing 104 supporting a rotating hub 105 and spindle 102 combination onto which the cartridge slips for rotating the cartridge. The spindle 102 includes a timing feature such as flat 102a which mates with a corresponding flat on the cartridge 110 to rotationally lock the cartridge in position on the spindle and ensure proper orientation and lockup of the cartridge. Spindle 102 is driven by an electric motor 103 supported by the housing 104 and configured to rotate the spindle in a single or opposing user-selectable directions. A power supply such as power cord 106 provides electric to the motor. In one embodiment, motor 103 may be a servo type motor with the hub directly mounted on top of it, but it could be any type of spindle with position sensing so the rotary machine 101 always knows real time rotational position of the cartridge 110 relative to the rotary machine. As non-limiting examples, an optical encoder or Hall Effect sensor may be used to automatically sense the rotational positon of the cartridge 110. This allows the machine to keep track of what reaction and property of the soil sample is positioned in what processing chamber. Rotary machine 101 may also be configured as and incorporate a colorimeter including a single or multiple light sources 192 (e.g. LEDs or other type lighting) to perform the color analysis of the samples while spinning or in a stopped and selectively indexed operating mode for detecting color.

Cartridge 110 is removably mounted on spindle 102 and rotated by the rotary machine 101 for processing soil samples in the manner further described herein. In some representative examples, the cartridge may be rotated or spun at speeds of about and including 5,000-15,000 rpm (revolutions per minute). Other speeds may be used.

Rotary machine 101 may include a programmable controller 191 in some embodiments for controlling the motor 103 and processing of samples including colorimetric analysis of the sample for various properties or analytes. The programmable controller 191 may includes a programmable processor, and computer readable medium which may include volatile memory and non-volatile memory operably and communicably coupled to the processor. The non-volatile memory may be any permanent or removable type memory such as a hard disk drive (HDD), solid-state drive (SDD), a removable SD card, USB drive, read-only memory (ROM), flash memory, ferroelectric RAM, and the like. Both the volatile memory and the non-volatile memory are used for saving data or results from processed samples, for storing programming (program instructions or software), and storing operating parameters associated with operation of the rotary machine 101 or processing samples, etc. Controller 191 may further include an input/output communication interface or module configured for wireless and/or wired communication for programming the processor and exchanging sampling results or other data with the rotary machine 101 via an external electronic device (e.g. computer, cell phone, tablet, laptop, etc.). Wireless communication protocols used may include Bluetooth, NFC (near field communication), Wi-Fi, or others. It is well within the ambit of one skilled in the art to provide and configure a controller with all the required appurtenances to provide a fully function control system for operating the rotary machine and processing soil samples in the manner disclosed herein.

The programmable controller 191 is programmable to control the rotary machine for spinning, rotating, and oscillating the cartridge 110 in the two different operating modes described above: the continuous single rotational direction for multiple complete revolutions for sample mixture distribution, or the back and forth oscillating motions in less than a full revolution for mixing contents of the processing chambers. The controller 191 is programmed to initiate each of these operating modes in a timed sequential manner in accordance with the sample processing methods disclosed elsewhere herein.

Referring now to FIGS. 1-17, the first embodiment of an analytical cartridge 110 comprises a plurality of processing cavities or chambers arranged in an array for processing multiple wetted soil samples simultaneously. Cartridge 110 is illustrated with a circular disk shape and includes a circular main body 111, a top cover 112, and an annular bottom cover 113 defined by a filter ring 140 in one embodiment attachable to the main body. While illustrated herein with a circular shape, cartridge 110 can have any shape that is balanced about centerline axis Cv. In other embodiments, cartridge 110 can be a polygon, a lemniscate, or a rose curve. In one embodiment, preferably at least the top cover 112 and filter ring 140 are made of a clear transparent plastic material. This allows the user see the contents of the multiple chambers when processing soil samples and importantly allows detection light from an external light source 192 of a colorimeter (e.g. LEDs) to be shone through reagent mixing chambers 124 (further described herein) for colorimetric detection of analytes in the sample supernatant deposited in these chambers (see, e.g. FIG. 34). An example of a suitable clear plastic material is Styrene Acrylonitrile (SAN) which possesses high clarity, chemical resistance, strength, and rigidity making this material suitable for withstanding centrifugal forces created by the rotary machine 101. In one embodiment, the top cover 112, filter ring 140, and intermediate main body 111 may all be formed of a clear material such as SAN so that the optical properties of these parts are consistent and don't skew the absorbance measurements recorded by the colorimeter.

Figure 2:
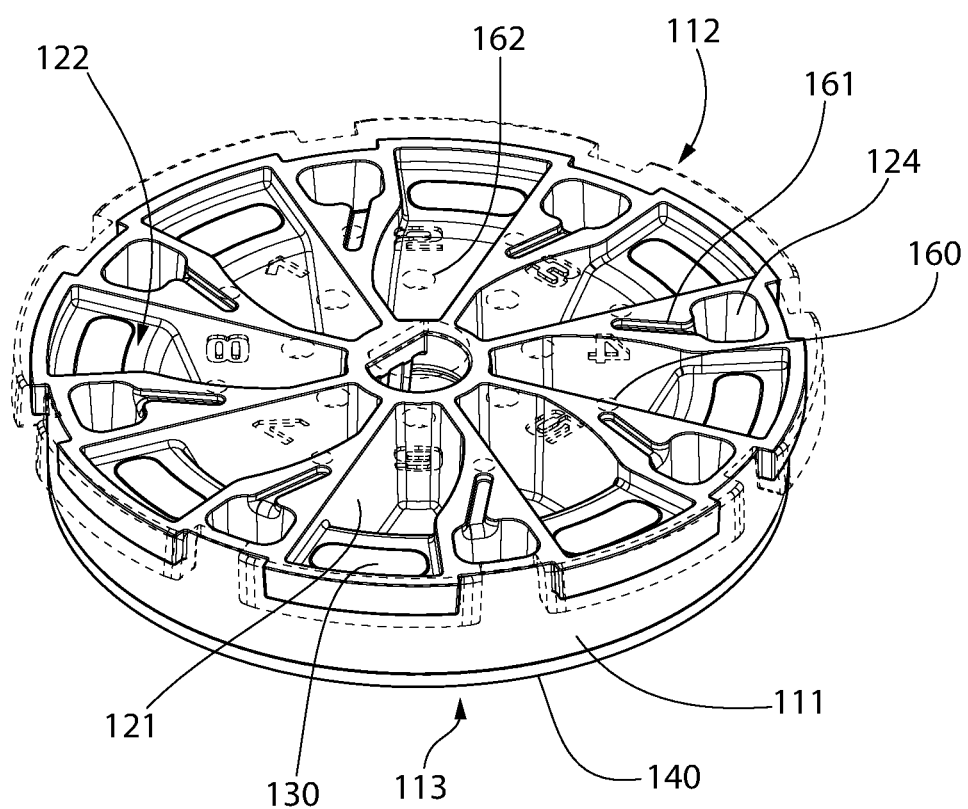
FIG. 2 is a perspective view thereof with cover shown in phantom lines to reveal interior processing chambers of the cartridge.
Figure 3:
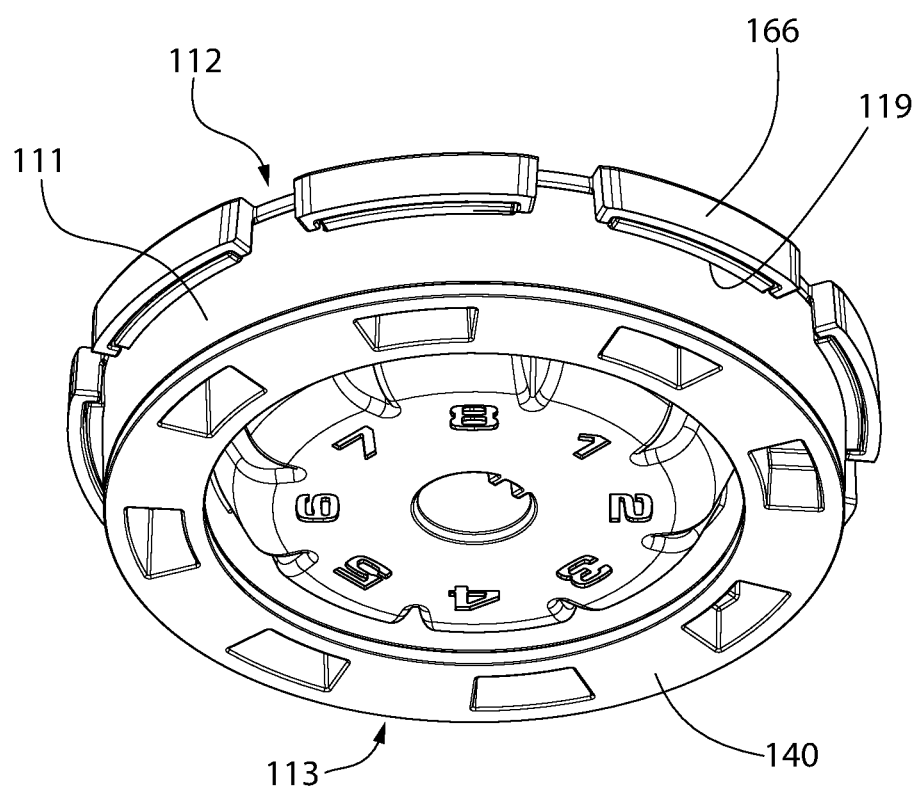
FIG. 3 is a bottom perspective view thereof.
Figure 4A:
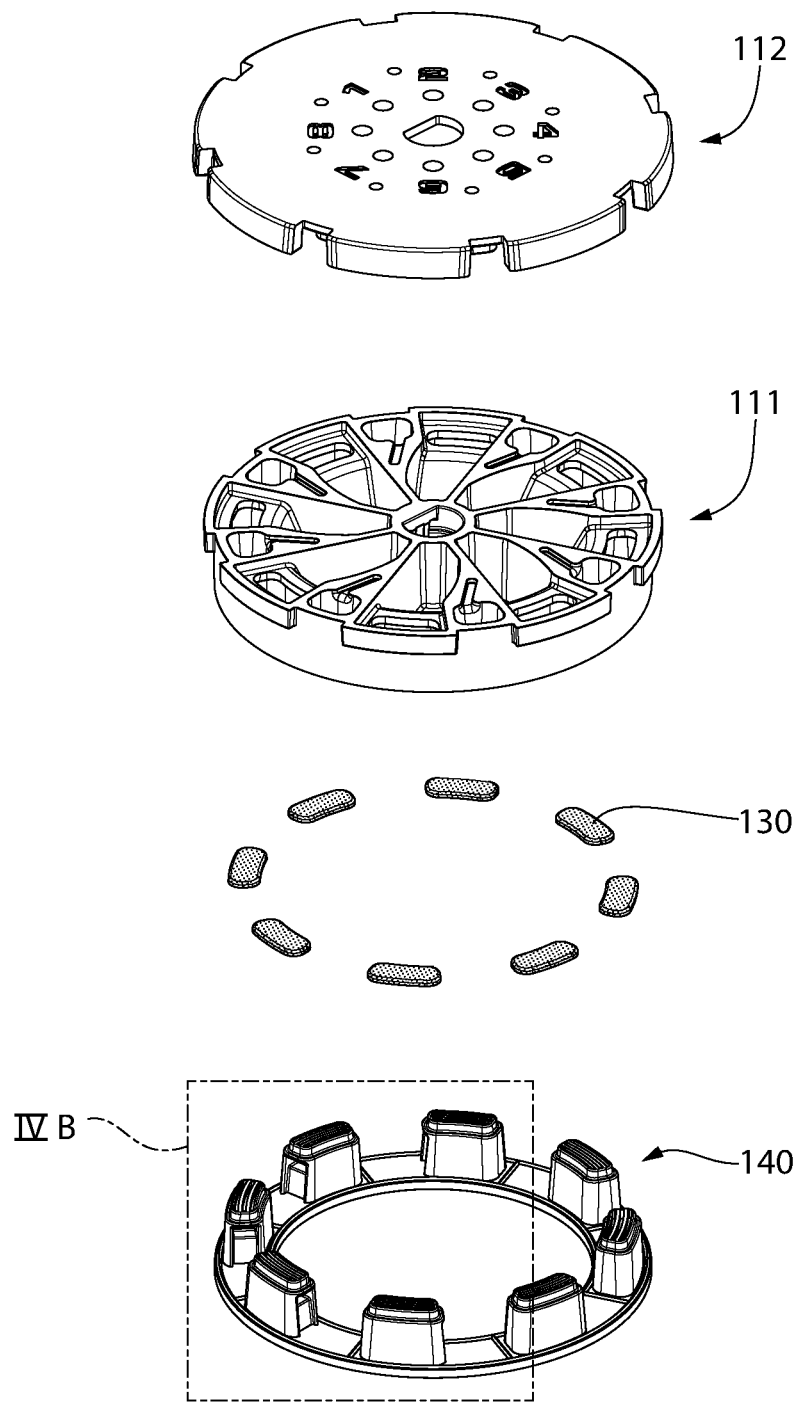
FIG. 4A is a top perspective exploded view thereof.
Figure 4B:
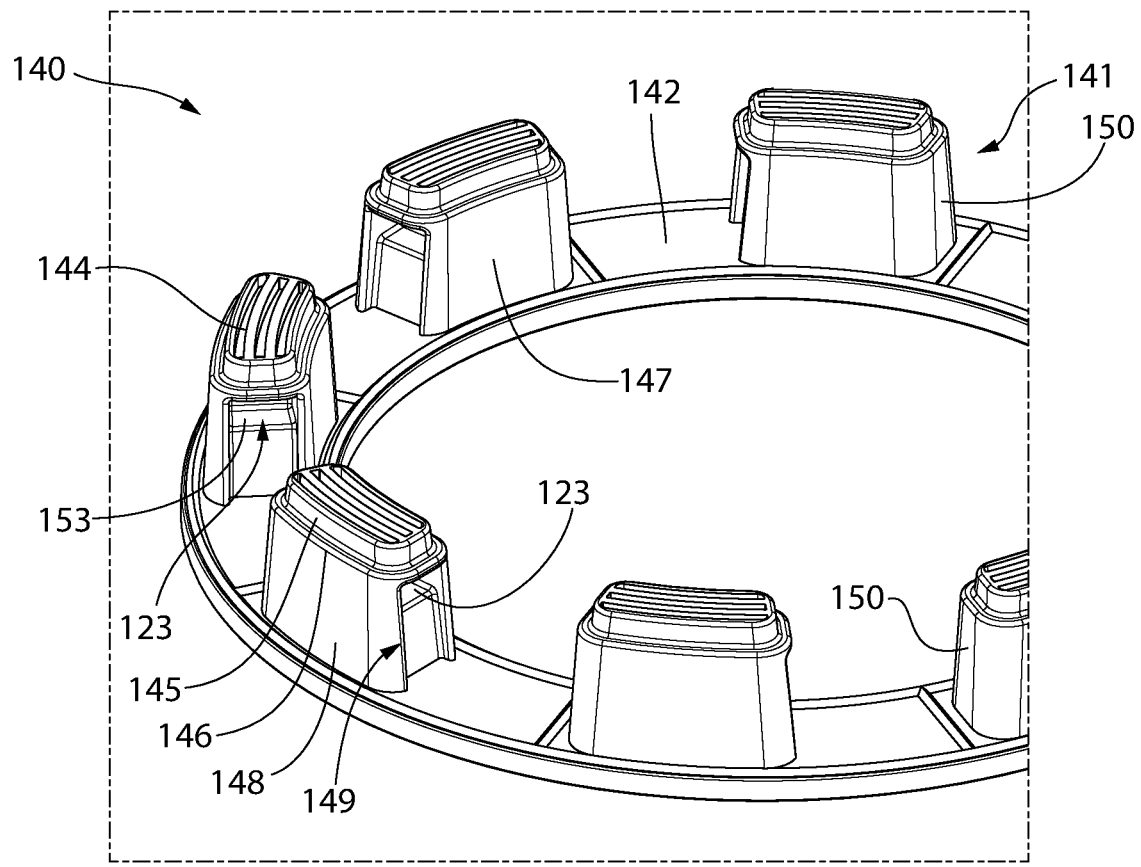
FIG. 4B is a detailed view of the filter ring shown in and taken from FIG. 4A.
Figure 5:
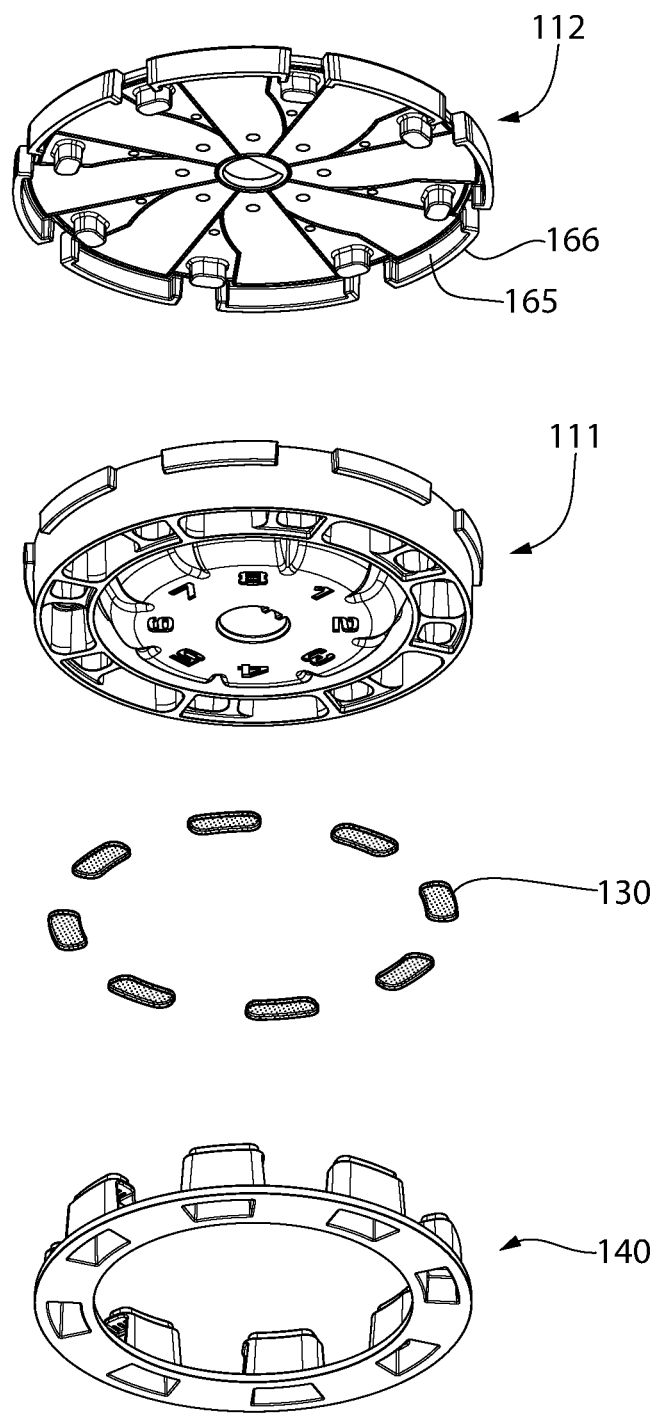
FIG. 5 is a bottom perspective exploded view thereof.
Figure 6:
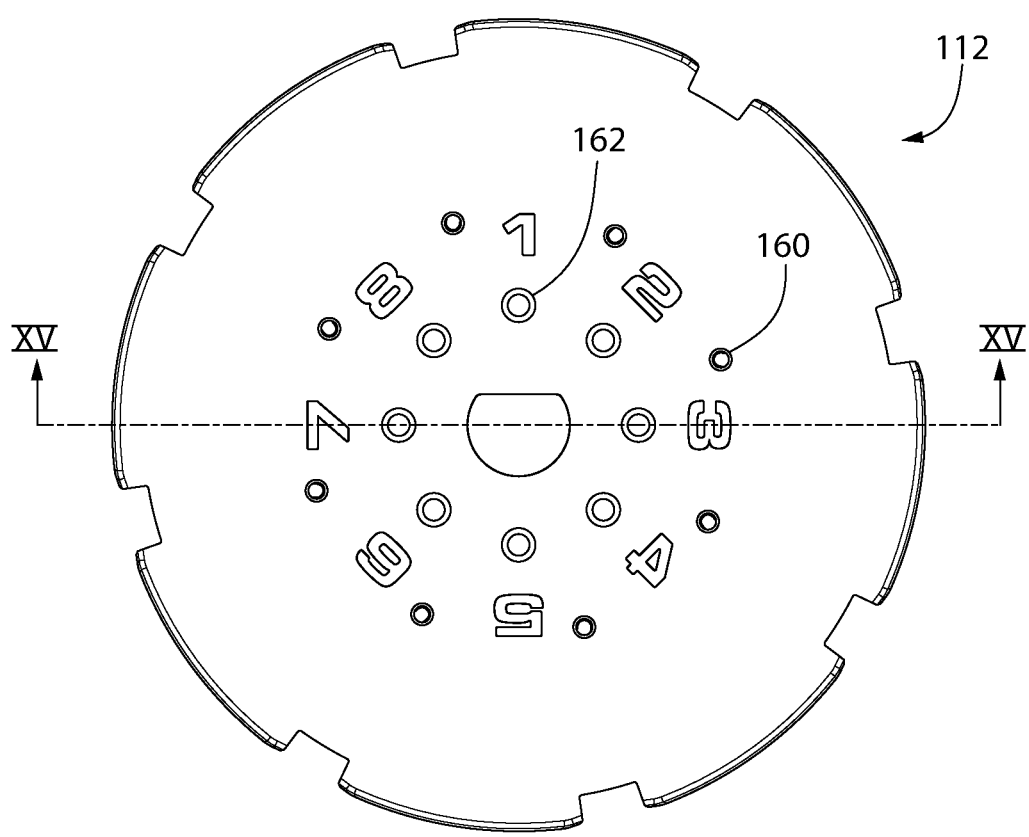
FIG. 6 is a top plan view thereof.
Figure 7:
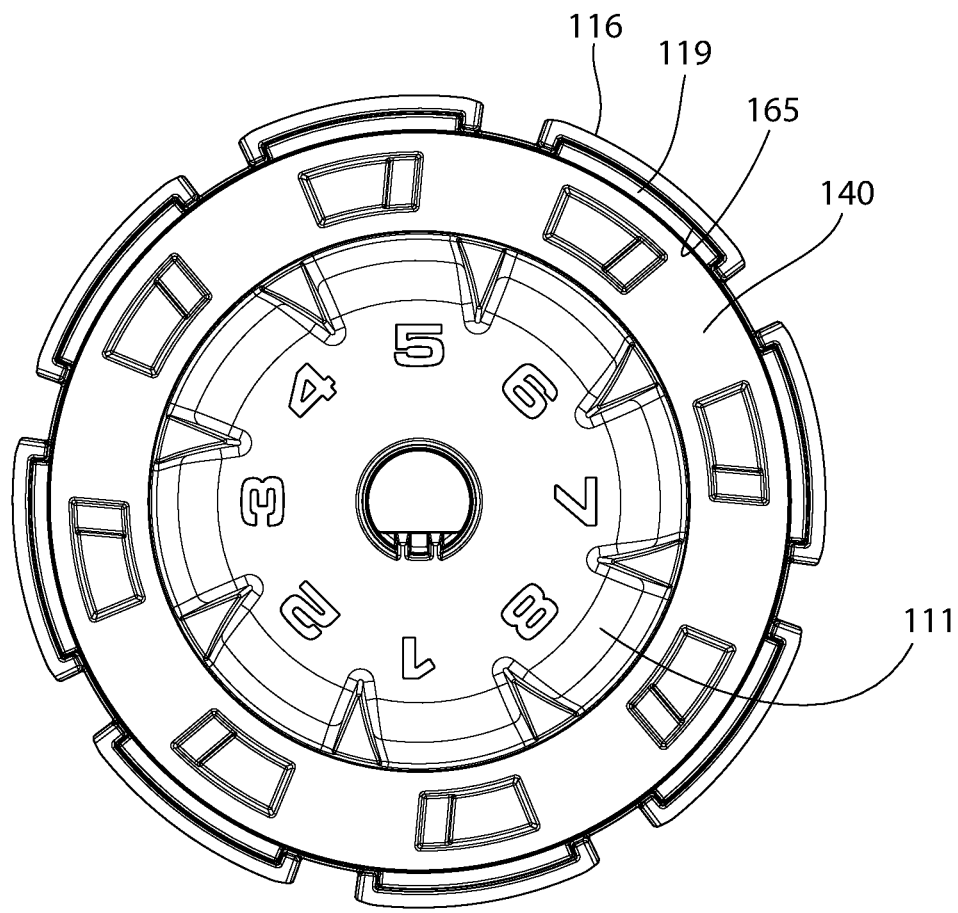
FIG. 7 is a bottom plan view thereof.
Figure 8:
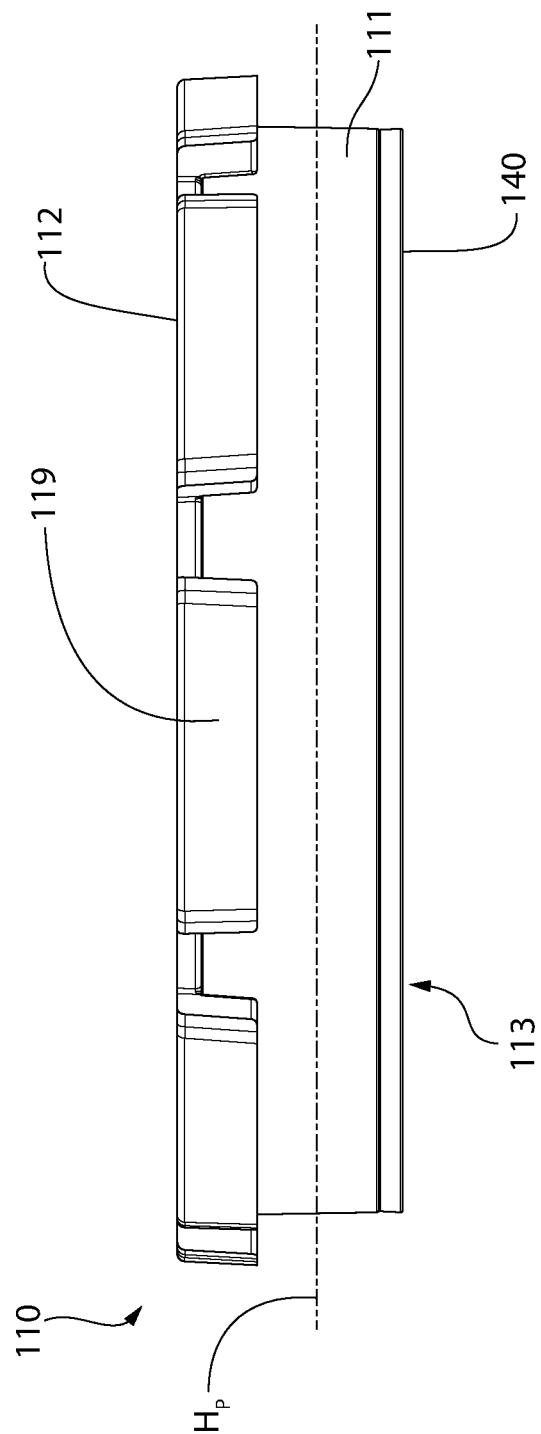
FIG. 8 is a side view thereof.

The cartridge body 111, top cover 112, and filter ring 140 may each be injection molded into the configurations and having the features shown. The molded top cover 112, and filter ring 140 (bottom cover 113) preferably may be permanently attached to the top and bottom of main body 111 by any suitable method. In one embodiment, ultrasonic welding may be used to permanently join these components; however, other suitable attachment means such as adhesives or other may be used in other embodiments. Permanent attachment provides a fluidly tight and leak-proof coupling of the covers to the main body 111. The ultrasonic welding may further be to join the components of the cartridge main body along seal lines which will fluidly isolate the chambers of each of the sample processing trains 120 from each other to prevent cross contamination. Accordingly, top cover 112 may be sealed welded along the perimeters of each of the chambers in each processing train 120 to accomplish this. An example of ultrasonic seal lines 190 for one processing train 120 is shown in FIG. 2 (recognizing that the chambers of all processing trains would be sealed with covered 112 in a similar manner).

Cartridge 110 defines vertical centerline axis Cv and a horizontal reference plane Hp extending horizontally and located midway between the top surface of the top cover 112 and bottom surface of the filter ring 140. Centerline axis Cv in turn defines an axis of rotation of the cartridge 110 when mounted on the spindle 103 of the rotary machine 101 which becomes coaxial with axis Cv. A central mounting opening 114 is formed at the centerline axis Cv for insertion of the spindle 102 of the rotary machine 101. Opening 114 is D-shaped in one embodiment and includes a flat 115 which engages the flat 102a formed on the spindle 102 of the rotary machine 101 to rotationally lock the cartridge in position relative to the spindle and machine. This ensures position lockup between the spindle 102 and cartridge for rotating the cartridge to process the soil samples.

Main body 111 of cartridge 110 includes a top surface 117, bottom surface 118, and annular sidewall 116 extending between the top and bottom surfaces. In one embodiment, sidewall 116 may extend parallel to vertical centerline axis CA and perpendicularly to the top and bottom surfaces. Sidewall 116 may have a solid construction in one embodiment.

In one embodiment, a plurality of radially-protruding arcuate flanges 119 may be integrally formed with the cartridge main body 111 which are spaced apart circumferentially around the sidewall 116 of the main body. The arcuate flanges 119 are received in mating downwardly open arcuate sockets 165 spaced apart perimetrically around the top cover 112. In one embodiment, the sockets 165 may be formed by the underside of a plurality of arcuate protrusions 166 extending radially outward from the peripheral edge of the top cover as shown. The protrusions 166 have an arc length slightly longer than their corresponding flanges 119. The flanges and sockets ensure proper orientation of the top cover 112 relative to the main body 111.

The various sample processing chambers of cartridge 110 will now be further described. Referring to FIGS. 1-17, the analytical cartridge 110 includes an array of fluidly isolated sample processing trains 120 arranged circumferentially around the cartridge. Each processing train 120 generally comprises in fluid communication an extractant mixing chamber 121, an upper slurry filtration chamber 122, a lower supernatant collection chamber 123, and a reagent mixing chamber 124. The listing of the chambers 121-124 is in order of the soil sample slurry and supernatant flow path starting from the initial innermost chamber 121 to the final chamber 124 of each sample processing train 120. In the illustrated embodiment, there are eight processing trains 120 shown; however, more or less trains may be used. The chambers associated with each processing train 120 are generally arranged in different sectors (eight sectors in this embodiment) of the disk-shaped analytical cartridge 110. The processing trains 120 may arbitrarily be assigned alphabetic and/or numeric designations. Indicia (e.g. 1, 2, 3, etc.) may therefore be provided in some embodiments on the top cover 112 and underside of the cartridge main body 111 for each train, as illustrated. This allows the user to easily keep track of the different analytes or chemical properties being detected in each sample processing train 120 (e.g. potassium, nitrogen, phosphorus, etc.).

In one configuration, the extractant mixing chamber 121, slurry filtration chamber 122, and supernatant collection chamber 123 of each of the sample processing trains 120 may be arranged and radially aligned along a respective radial reference axis Rn of the train, where "n" equals the train number such as $R_1$, $R_2$, $R_3$, etc.). Reference axes Rn of each processing trains 120 shown in FIG. 11 passes through the center of an arcuate flange 119 of the cartridge main body 111. Portions of chambers 121, 122, and 123 fall on each side of its respective reference axis Rn. In the present embodiment, the mixing chamber 121 and slurry filtration chamber 122 may conveniently share a common upwardly open recess molded into the main body 111 of the cartridge 110 as shown. This advantageously facilitates sealing attaching the cover 112 to the main body 111 of cartridge 110 and minimizes the number of ultrasonic seal lines 190 required for one processing train 120. Thought of another way, the slurry filtration chamber 122 may be considered to define a radially outward shallower portion of the extractant mixing chamber 121 than the deeper inward extractant mixing portion (see, e.g. FIG. 14).

Extractant mixing chambers 121 are radially elongated and include a circumferential inner wall 127 nearest central mounting opening 114, an opposing circumferential outer wall 128, a pair of opposing vertical radial walls 129, and a horizontal bottom wall 126. The top of mixing chamber 121 is open and closed by the top cover 112 when attached to the main body 111 of the cartridge 110. Radial walls 129 may be non-parallel in one embodiment and gradually diverge moving outwards from the vertical centerline axis Cv of the cartridge forming a wedge shaped chamber. In the non-limiting illustrated embodiment, one of the radial walls 129 of the extractant mixing chamber 121 may be radially straight and lies on a radius line RL of the circular shaped cartridge main body 111. The other opposing radial wall 129 may be concavely curved which may promote better mixing.

In one embodiment, inner wall 127 of extractant mixing chamber 121 may have a substantially vertical orientation and the outer wall 128 may be obliquely inclined and angled relative to the vertical centerline axis Cv of the cartridge 110. Outer wall 128 defines an upwards sloping surface (moving from the bottom wall 128 outwards to the top of the mixing chamber 121) and leads to the slurry filtration chamber 122 positioned radially outwards from the extractant mixing chamber 121. Outer wall 128 is disposed at oblique angle A1 to vertical centerline axis Cv, which in some representative non-limiting examples may be between about and including 10 to 80 degrees, and preferably between about and including 20-45 degrees. The sloped outer wall 128 facilitates the outward flow of the extractant and soil slurry mixture from the extractant mixing chamber 121 to the radially outer slurry filtration chamber 122 by centrifugal force when the cartridge 110 is rotated or spun by the rotary machine 101.

Slurry filtration chamber 122 may be vertically positioned on top of the supernatant collection chamber 123 in a stacked manner in one embodiment of the cartridge 110 as shown. Supernatant collection chamber 123 may be relatively smaller in volume than the extractant or reagent mixing chambers 121, 124 and serves a temporary plenum for collecting and allowing the supernatant to continue flowing towards and be deposited in the reagent mixing chambers.

A horizontally oriented sediment filter 130 disposed at the bottom of the upper slurry filtration chamber 122 separates that chamber from the lower supernatant collection chamber 123 which are fluidly connected through the filter. Filters 130 may be circumferentially elongated and oblong ovals in one embodiment, and may be slightly arcuately shaped (in top plan view) to comport with the circular shape of the cartridge 110. A plurality of filters 122 are provided and arranged along the same reference circle in circumferentially spaced apart relationship. Each extractant mixing chamber 121 has an associated sediment filter 130 positioned radially outwards therefrom as shown. Filter 122 automatically deliquifies (i.e. dewaters and removes dissolved/suspended matter in the water) the slurry by filtering out or trapping soil particles above a predetermined size from the extractant-slurry mixture using centrifugal force created by rotating/spinning the cartridge 110 with rotary machine 101. The resulting filtered and substantially visually clear liquid passing through filter referred to "supernatant" flows downwards through the filter 130 and is collected in the supernatant collection chamber 123 below. In one non-limiting example, sediment filters 130 used may be about 0.5 to 1 micron filters having openings sized to prevent passage of particles larger than the rated opening sizes; however, other suitable size filters may be used. In some embodiment, filters 130 may be pliable filter paper like in construction and made of Teflon, polyphenylene sulfide (PPS), or other materials as some non-limiting examples.

To prevent blinding the sediment filters 122 with the soil particles in the extractant-slurry mixture, each slurry filtration chamber 122 includes an integrally formed sludge trap such as sludge collection area 170. Sludge collection area 170 is positioned radially outward from the sediment filters 130 and represents the outermost peripheral portion of the slurry filtration chamber 122. In operation when the cartridge 110 is rotated or spun, the deliquified thickened sediment sludge remaining above the filter 130 which contains highly concentrated solids is forced radially outwards by centrifugal force to collect in the sludge collection area 170. The sludge collection area 170 has a solid circumferential vertical outer wall 171, two solid opposing vertical radial end walls 172, and a horizontal solid floor 173 as shown. Collection area 170 has sufficient volume to at least receive and contain the sludge produced during processing of a single soil sample in the rotary analytical cartridge 110.

In one embodiment, the filters 130 may be detachably mounted on a separate annular filter ring 140 insertable into and attachable to the cartridge main body 111 from below. Filter ring 140 includes a plurality of protruding filter housings 141 (aka drumheads) projecting upwards from an annular mounting base 142 of the ring. Housings 141 are circumferentially spaced apart on the base 142 as shown. The filter housings 141 are insertable upwardly into downwardly open receptacles 143 formed in cartridge main body 111 when the filter ring 140 is attached thereto from beneath the body. Receptacles 143 are further upwardly open for exposing the tops of the filter housings 141 to the slurry filtration chambers 122.

Each filter housing 141 is arcuately elongated and oblong in configuration having a pseudo-rectangular cuboid configuration comprising arcuately curved and parallel inner and outer walls 147, 148, an open radial end wall 149, and an opposing closed radial end wall 150. The supernatant collection chambers 123 may be formed as an integral unitary structural part of the raised filter housings 141 as shown. The open radial end wall 149 allows supernatant to flow from the collection chamber 123 to the reagent mixing chambers 124 as further described herein.

For mounting the filters 130 to the filter ring 140, each filter housing 141 may be terminated at its top end with a stepped shoulder 146 that defines an inwardly recessed filter retention rim 145 having an oblong annular configuration complementary configured to filters 130. The filters 130 each include a downwardly extending oblong annular lip 131 which slips over and engage the retention rims 145 of the filter housings 141. Filters 130 thus have an inverted U-shape in transverse cross-section in this example embodiment. The top surface of each housing 141 structure may be slotted in one embodiment including a plurality of arcuately curved, parallel, and elongated slots 144 which allow passage of supernatant from the slurry filtration chamber 122 down into the supernatant collection chambers 123 below the filter 130 in the filter housing 141. The solid portions of the top surface of the filter housings 141 between the spaced apart slots 144 provide support for the filters 130. In other possible embodiments, the top of the filter housings 141 may be completed open without slots 144 and solid portions.

Use of the annular filter ring 140 advantageously allow the filters to be completely preassembled onto the filter housings 141 outside of the main body 111 of the analytical cartridge 110, thereby greatly facilitating assembly of the cartridge. In other possible embodiments contemplated, however, the filter ring and housing structure may be omitted and the filters 130 may instead be mounted in similar structure molded integrally with the cartridge main body 111.

The reagent mixing chambers 124 may be angularly and laterally (i.e. circumferentially) offset from the radial reference axes Rn and the supernatant collection chambers 123. Mixing chambers 124 are interspersed between each set of an upper slurry filtration chamber 122 and corresponding lower supernatant collection chamber 123. The mixing chambers 124 may be located laterally adjacent to and spaced apart from the supernatant collection chambers 123 in one configuration of cartridge main body 111. Pairs of mixing chambers 124 and supernatant collection chambers 123 may be arranged perimetrically around the outer peripheral portion of the cartridge 110 disposed proximate to the annular peripheral edge 125 of the cartridge main body 111 defined by the sidewall 116. Chambers 123 and 124 may therefore be located on the same imaginary reference circle of the cartridge. In the present arrangement shown, the slurry filtration chamber 122, supernatant collection chamber 123, and mixing chambers 124 are located radially outwards from the extractant mixing chambers 121. The extractant mixing chambers 121 and reagent mixing chambers 124 may extend for a majority of the full height of the cartridge main body 111.

Figure 17:
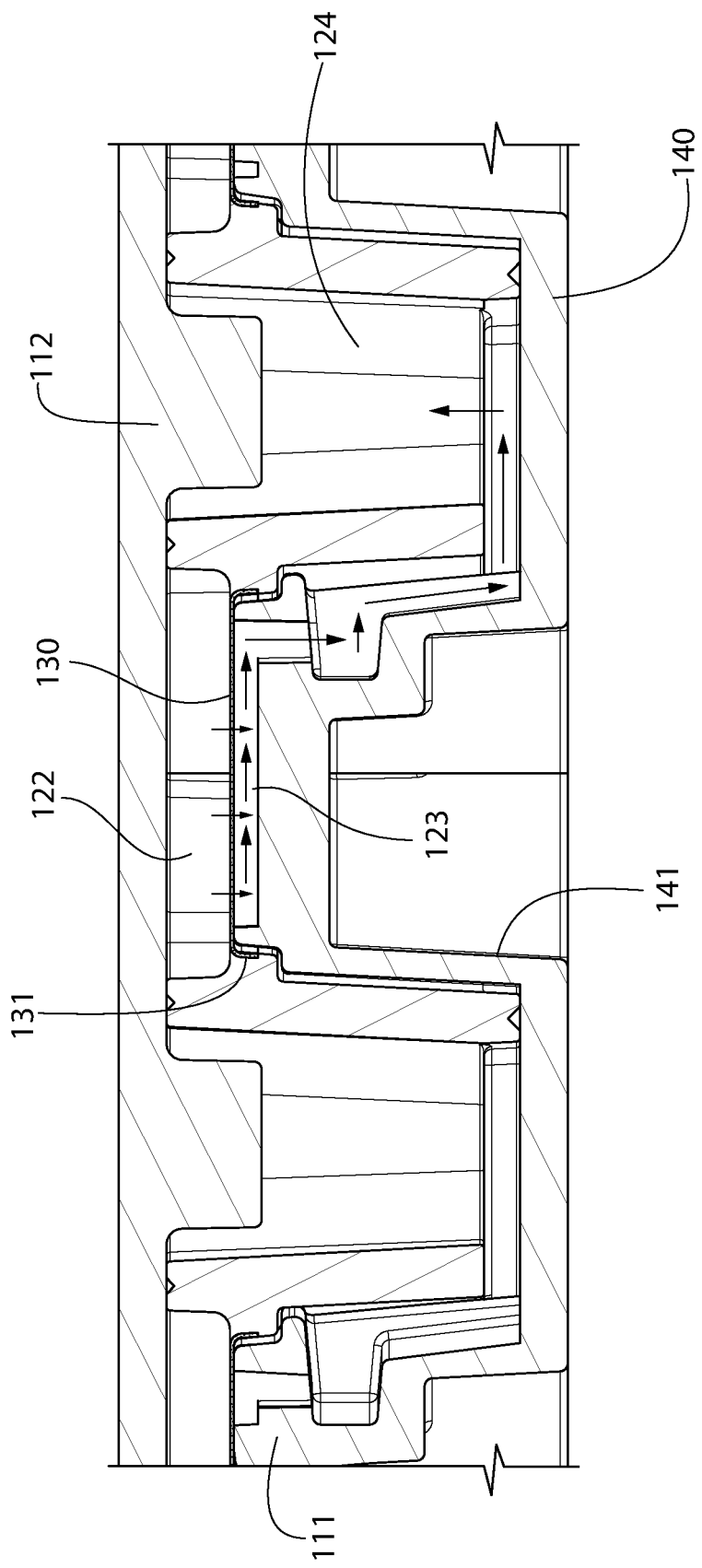
FIG. 17 is a transverse cross sectional view taken from FIG. 11.
Figure 18:
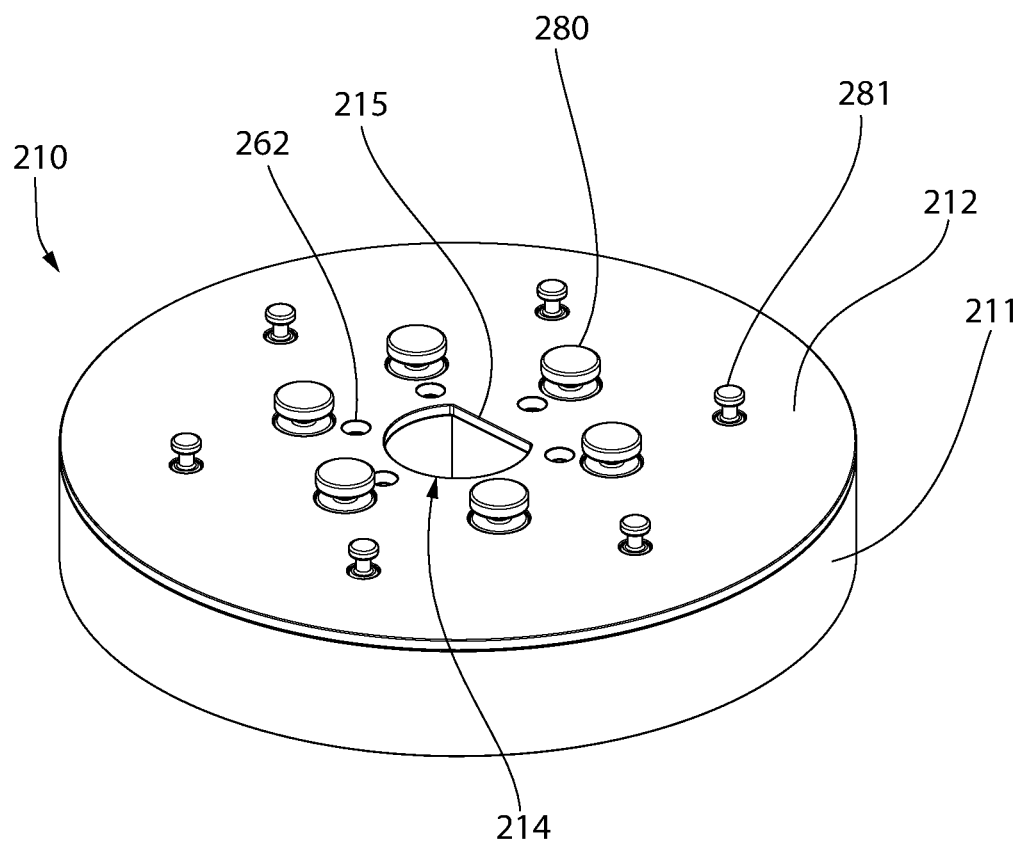
FIG. 18 is a top perspective view of a second analytical cartridge usable for soil testing according to the present disclosure.
Figure 19:
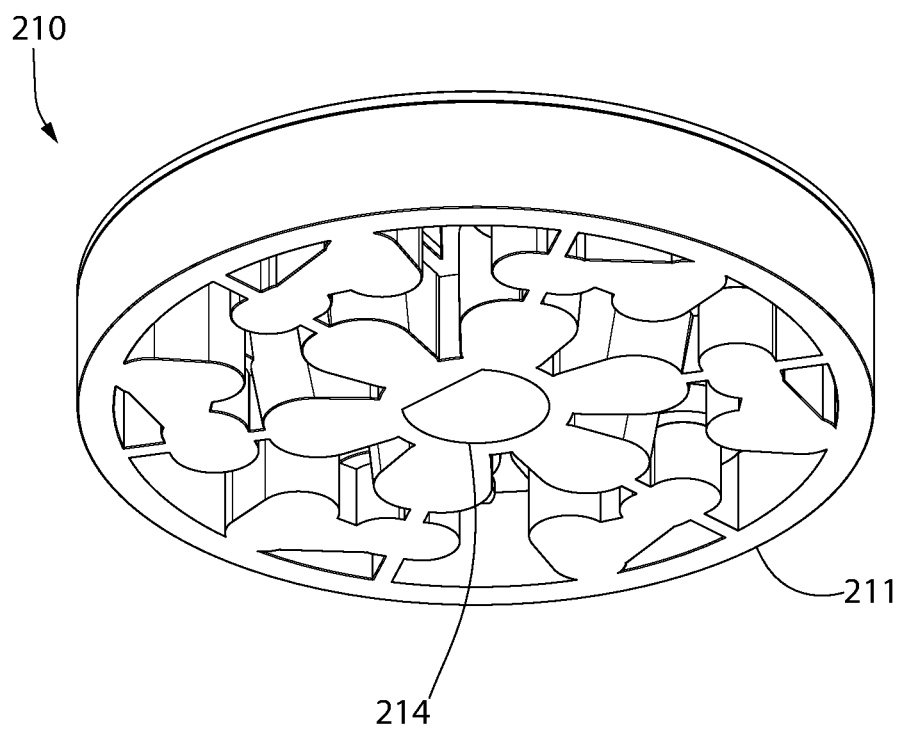
FIG. 19 is a bottom perspective view thereof.
Figure 20:
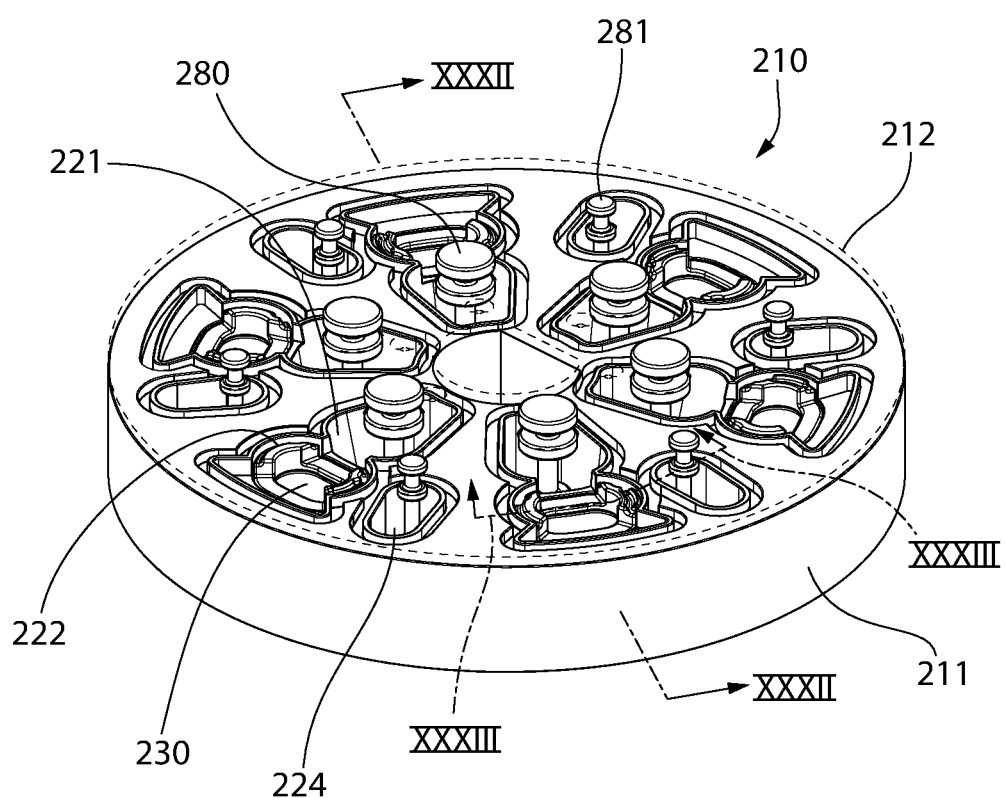
FIG. 20 is a perspective view thereof with cover shown in phantom lines to reveal interior processing chambers of the cartridge.
Figure 21A:
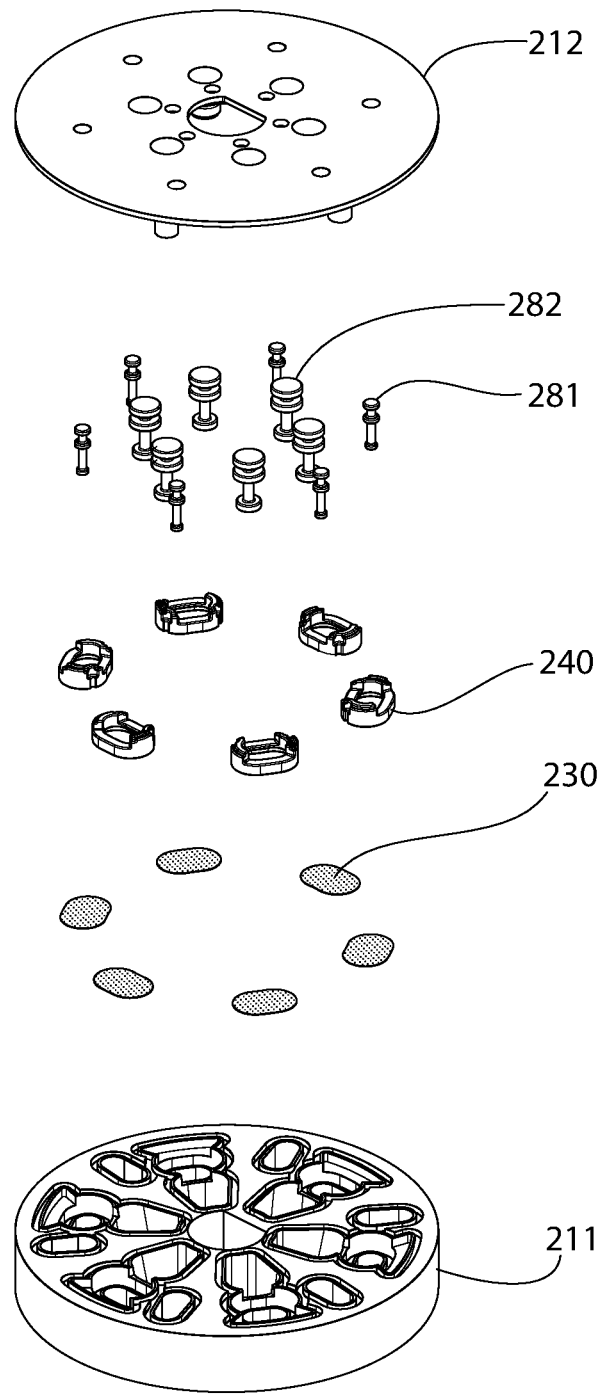
FIG. 21A is a top perspective exploded view thereof.
Figure 21B:
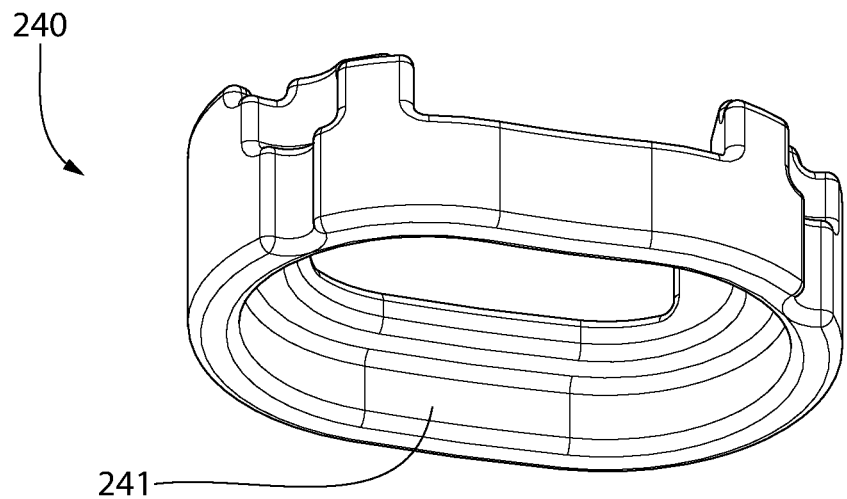
FIGS. 21B and 21C are bottom and top perspective views of a filter retention ring shown in and taken from FIG. 21A.
Figure 21C:
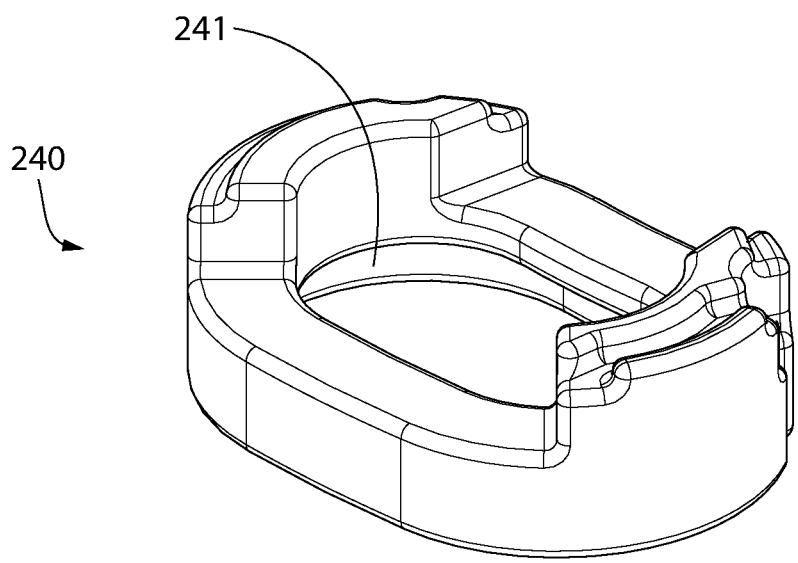
Figure 22:
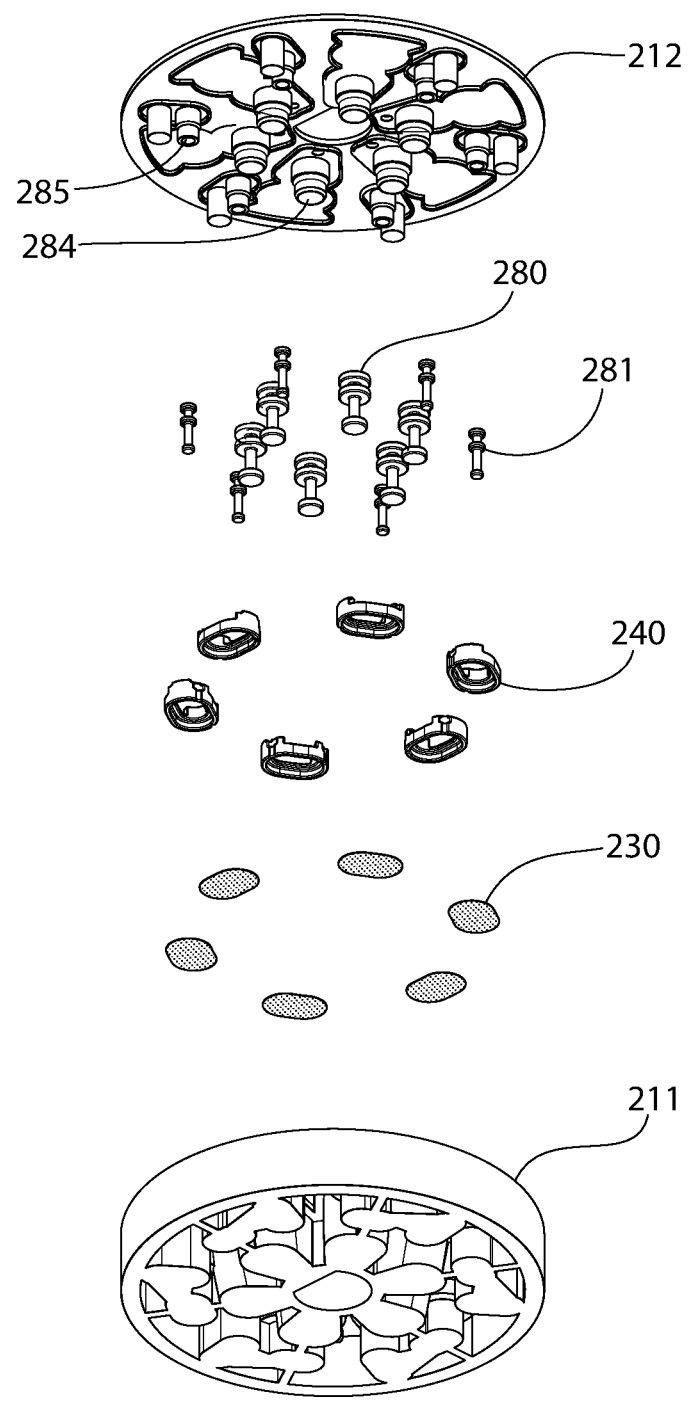
FIG. 22 is a bottom perspective exploded view thereof.
Figure 23:
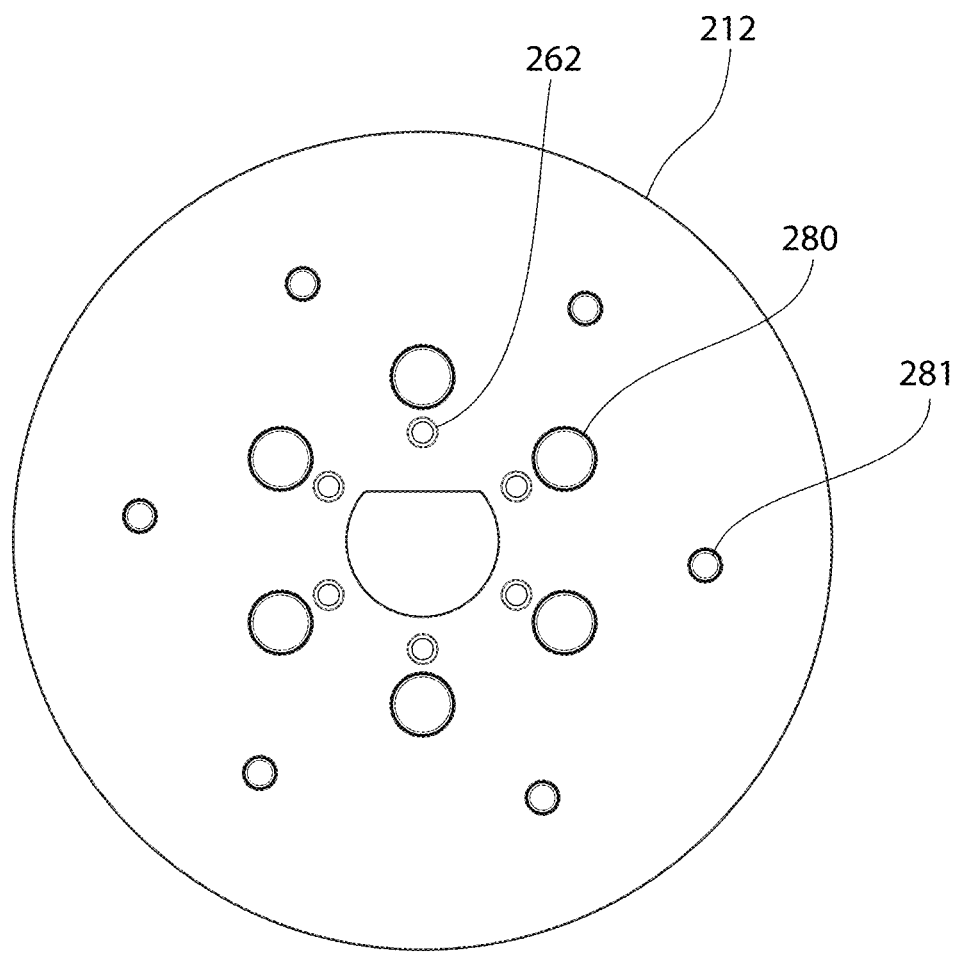
FIG. 23 is a top plan view thereof.
Figure 24:
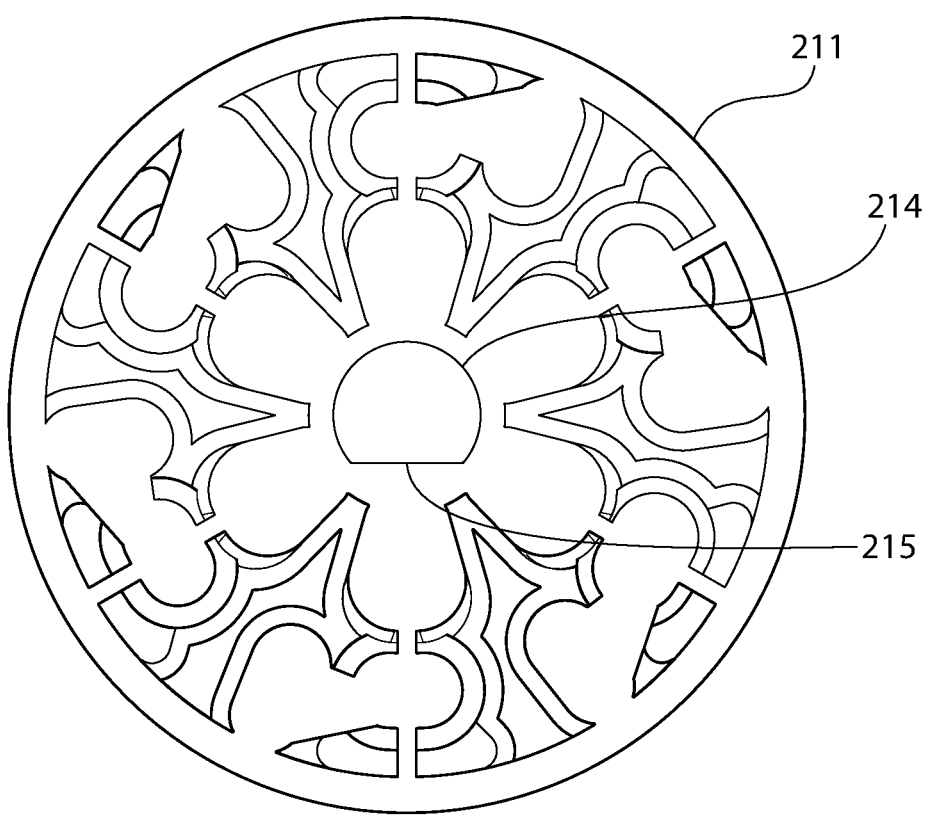
FIG. 24 is a bottom plan view thereof.
Figure 25:
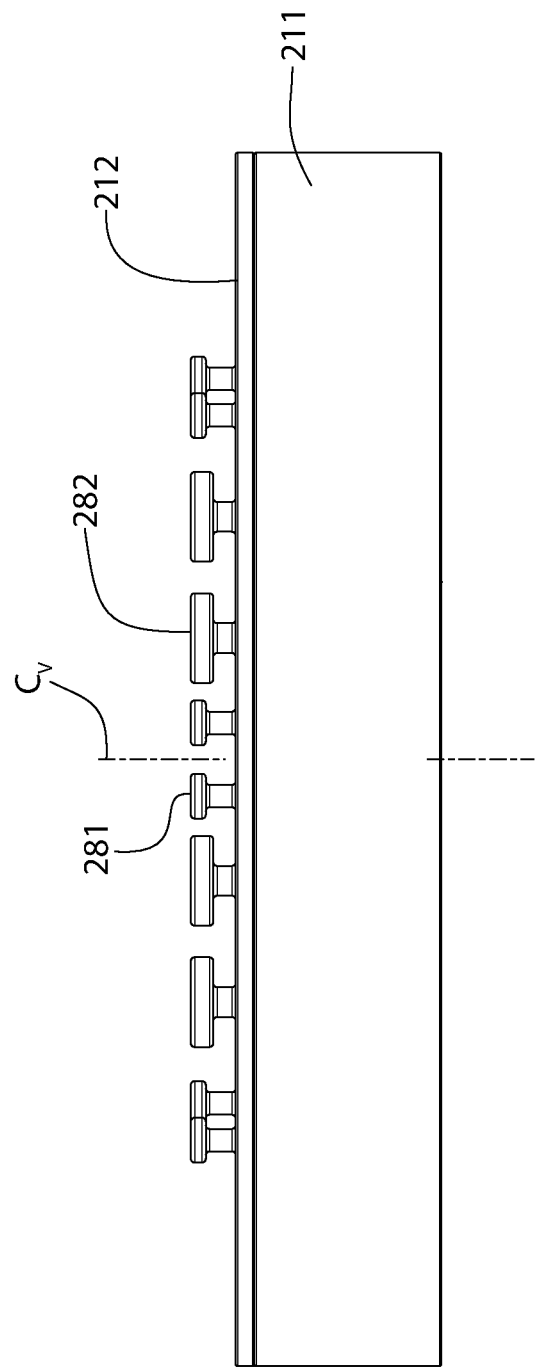
FIG. 25 is a side view thereof.
Figure 26:
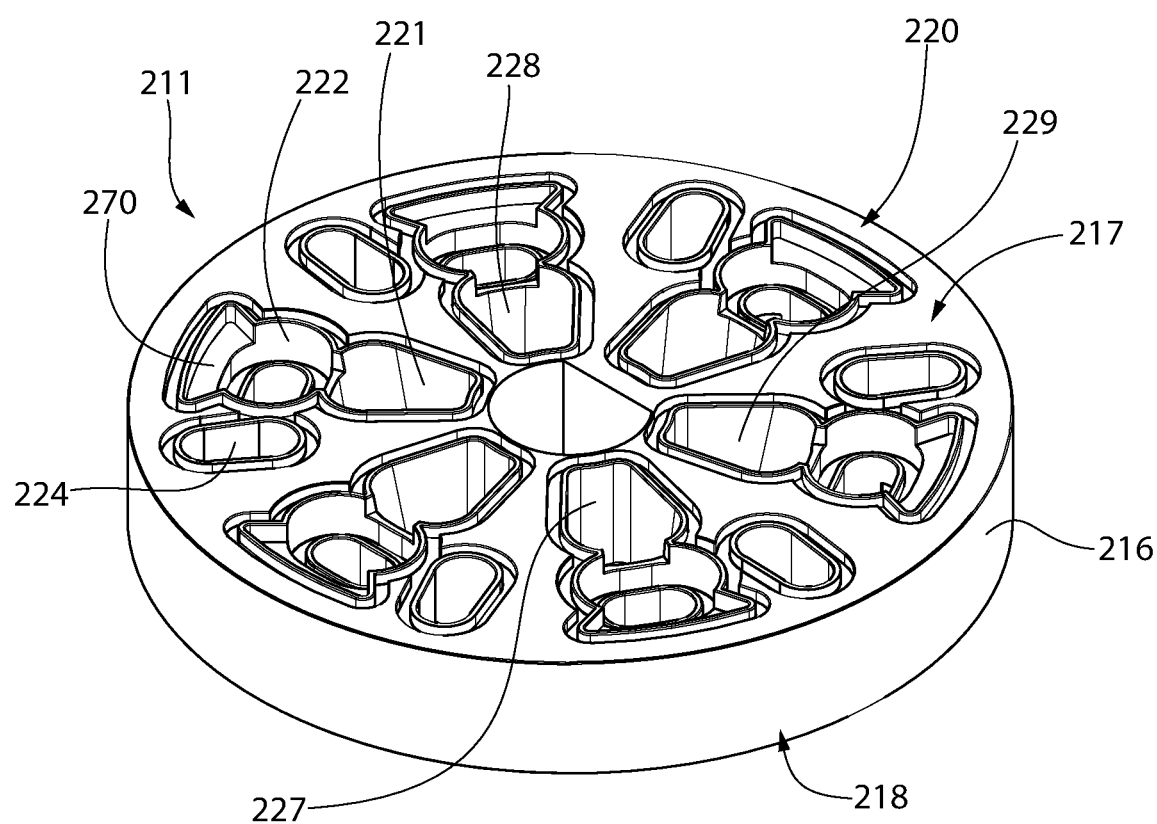
FIG. 26 is a top perspective view of the main body of the cartridge of FIG. 18.
Figure 27:
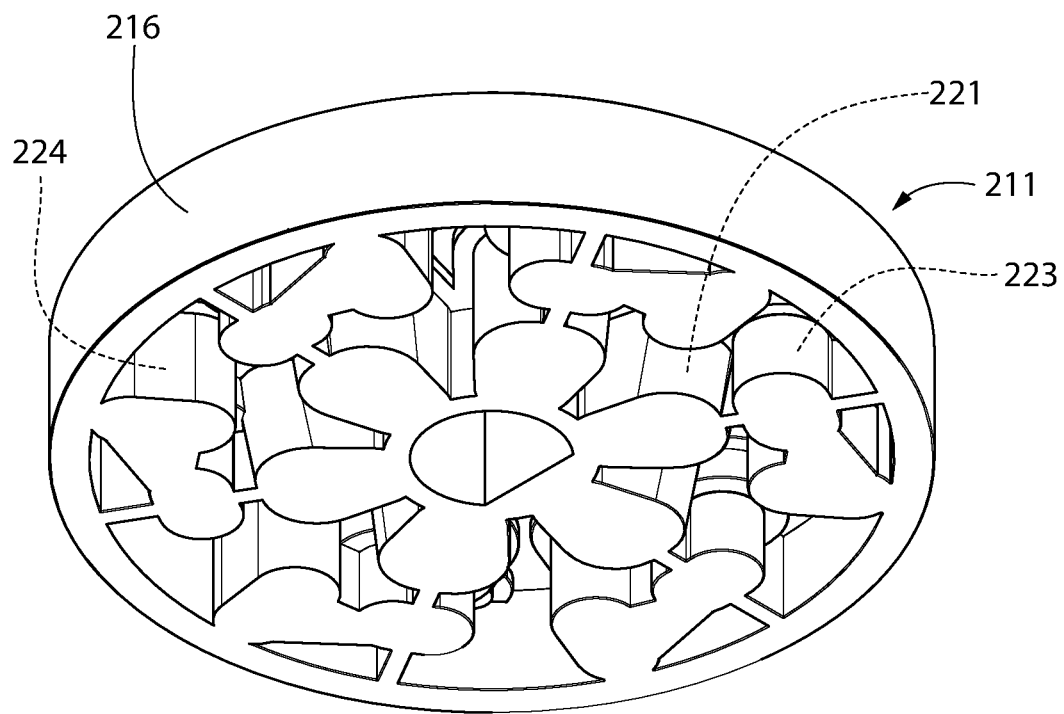
FIG. 27 is a bottom perspective view thereof.
Figure 28:
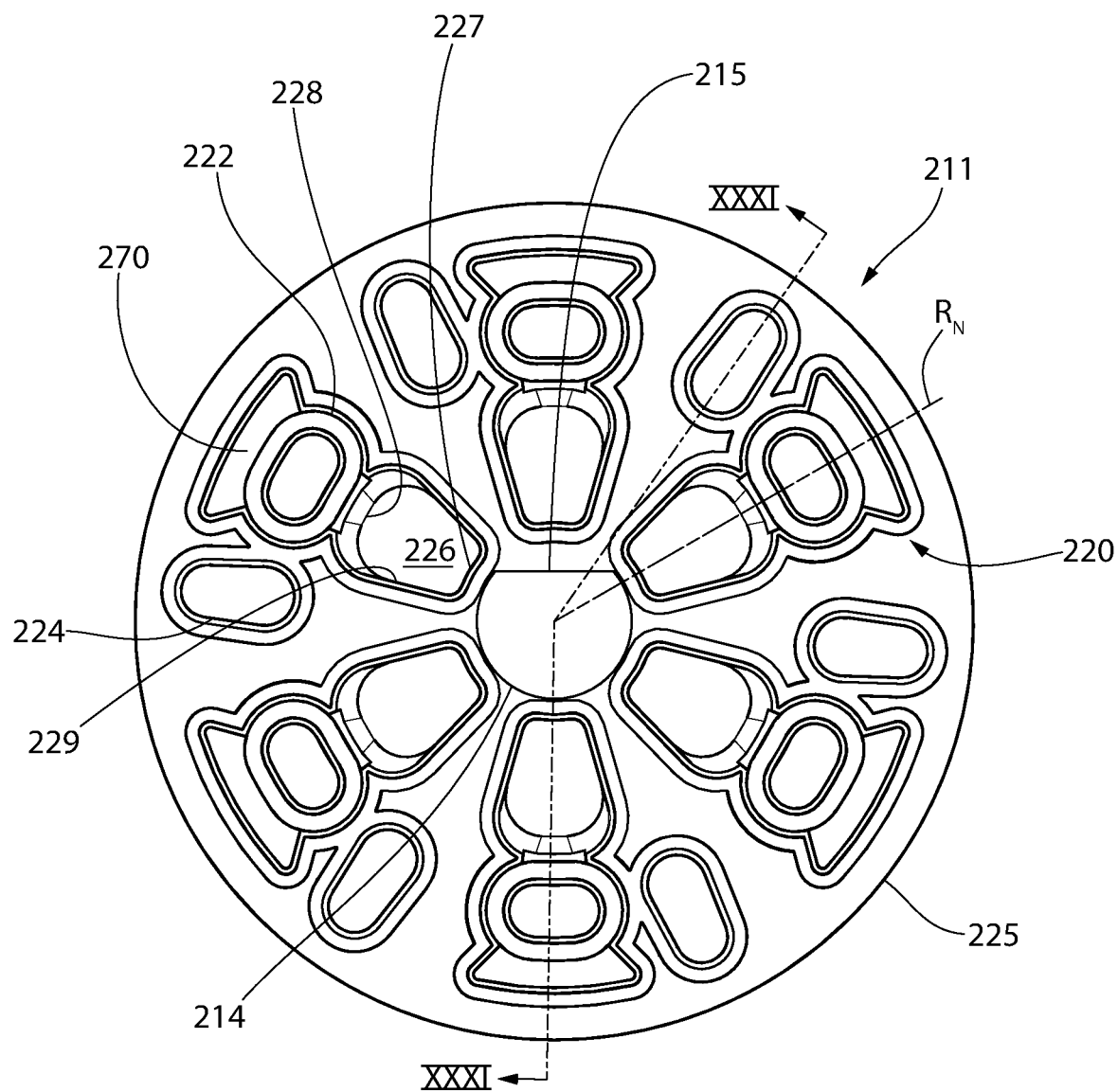
FIG. 28 is a top plan view thereof.
Figure 29:
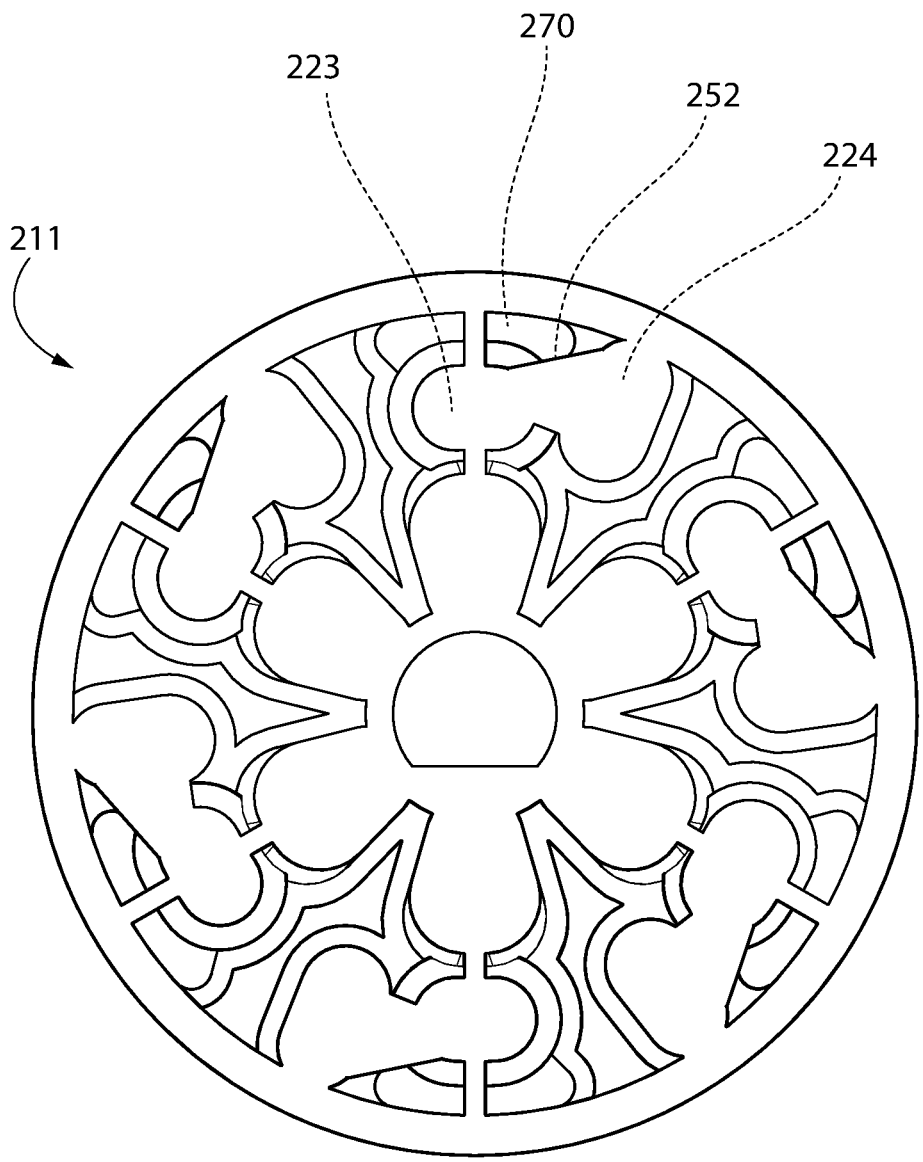
FIG. 29 is a bottom plan view thereof.
Figure 30:
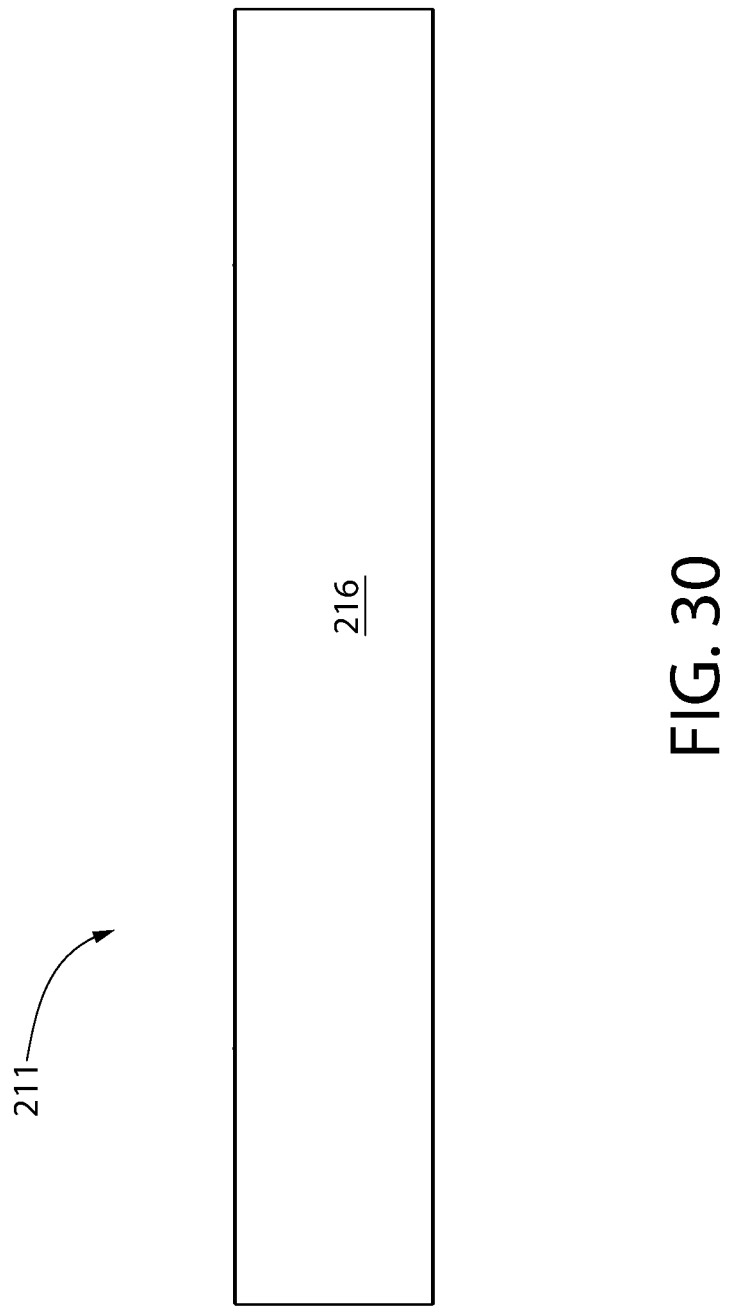
FIG. 30 is a side view thereof.
Figure 31:
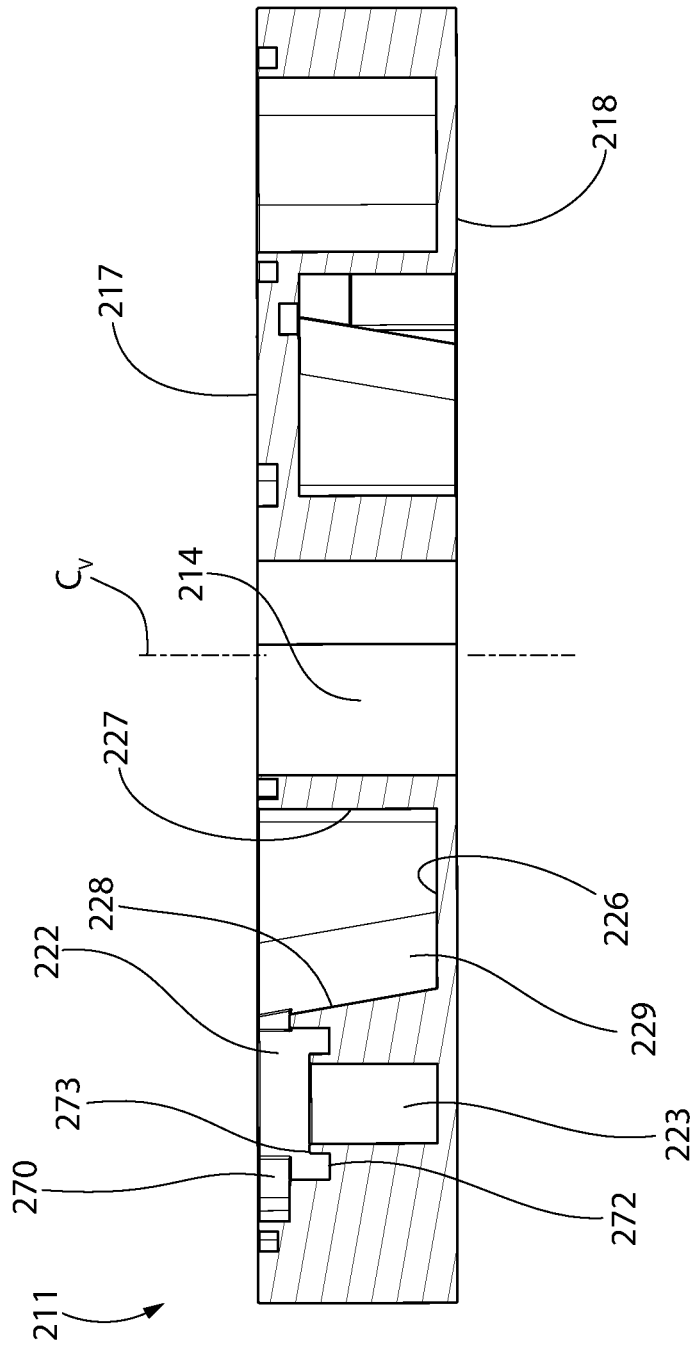
FIG. 31 is a transverse cross-sectional view thereof taken from FIG. 28 from phantom section line XXXI.

Referring to FIG. 17, the supernatant collection chambers 123 are each fluidly connected to a respective reagent mixing chambers 124 via a laterally and circumferentially extending flow passage 152. Flow passage 152 may have a circuitous multi-stepped configuration in one non-limiting embodiment so that there is no straight line of sight between chambers 123 and 124. This inhibits backflow of supernatant from the mixing chambers 124 into the collections chamber 123 when the cartridge 110 is spun by the rotary machine 101. In other embodiments, a more straight fluid passage configuration may be used. In one embodiment, the floor 153 of the supernatant collection chamber 123 may be spaced apart from and elevated above bottom surface 118 of the cartridge main body 111. The floor 153 of collection chamber 123 may also be elevated above the floor 154 of the mixing chamber 124 which is formed by the filter ring 140 for the same purpose. Supernatant flow from collection chamber 123 to mixing chamber 124 is lateral and downwards.

Each reagent mixing chamber 124 has an associated reagent fill hole 160 formed through the top cover 112 for the addition of reagent to the supernatant in chamber 124. The fill holes 160 may be spaced radially inwards of the detections chambers 124. Each fill hole 160 is fluidly connected to its mixing chamber 124 by a reagent injection conduit 161 which extends radially between the chamber and fill hole. The injection conduits 161 may be located proximate to the top surface 117 of the cartridge main body 110 and penetrate the top surface as shown. Each injection conduit in some embodiments may further be elevated above the floor 154 of the mixing chamber 124 to inhibit backflow of supernatant from the chamber to the fill hole 160 when the cartridge 110 is spun by the rotary machine 101.

The top cover 112 further includes a plurality of soil sample slurry fill holes 162 which open into the extractant mixing chambers 121. This permits the mixture of soil slurry and extractant to be injected into each mixing chamber 121 for complete mixing to extract the analyte from the mixture. Fill holes 162 may be located radially inwards of the reagent fill holes 160 and are circumferentially spaced apart proximate to the central mounting opening 114 of the cartridge 110 as shown.

Figure 9:
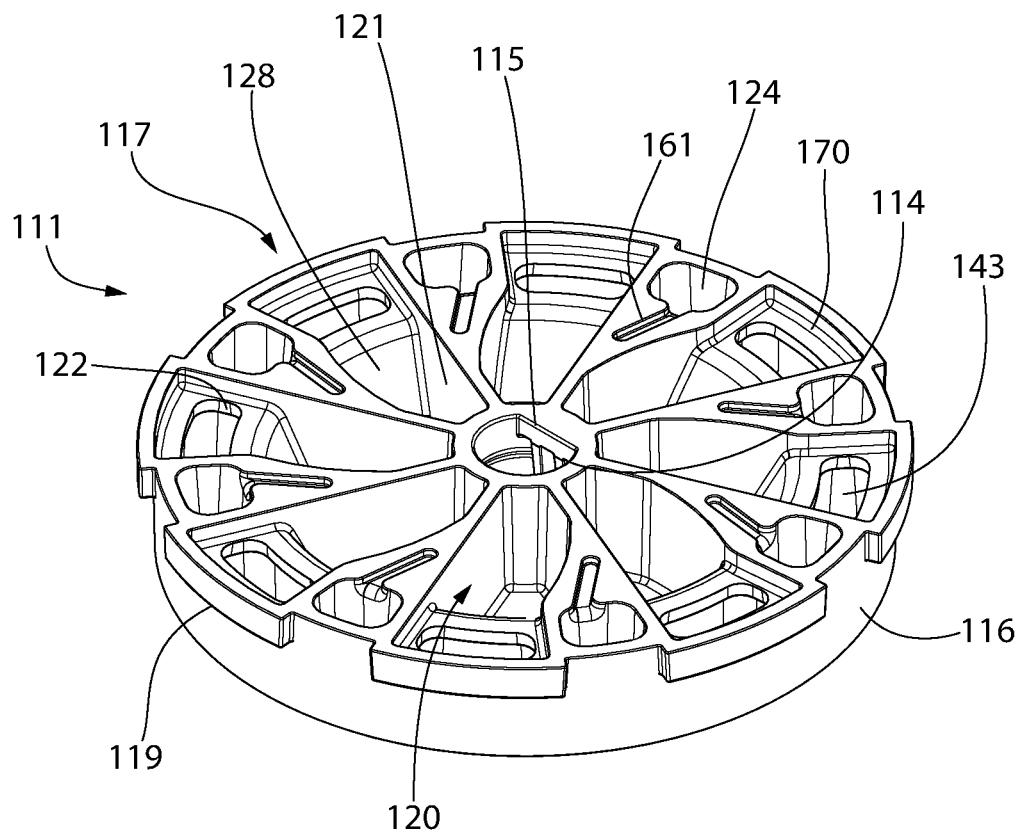
FIG. 9 is a top perspective view of the main body of the cartridge of FIG. 1.
Figure 10:
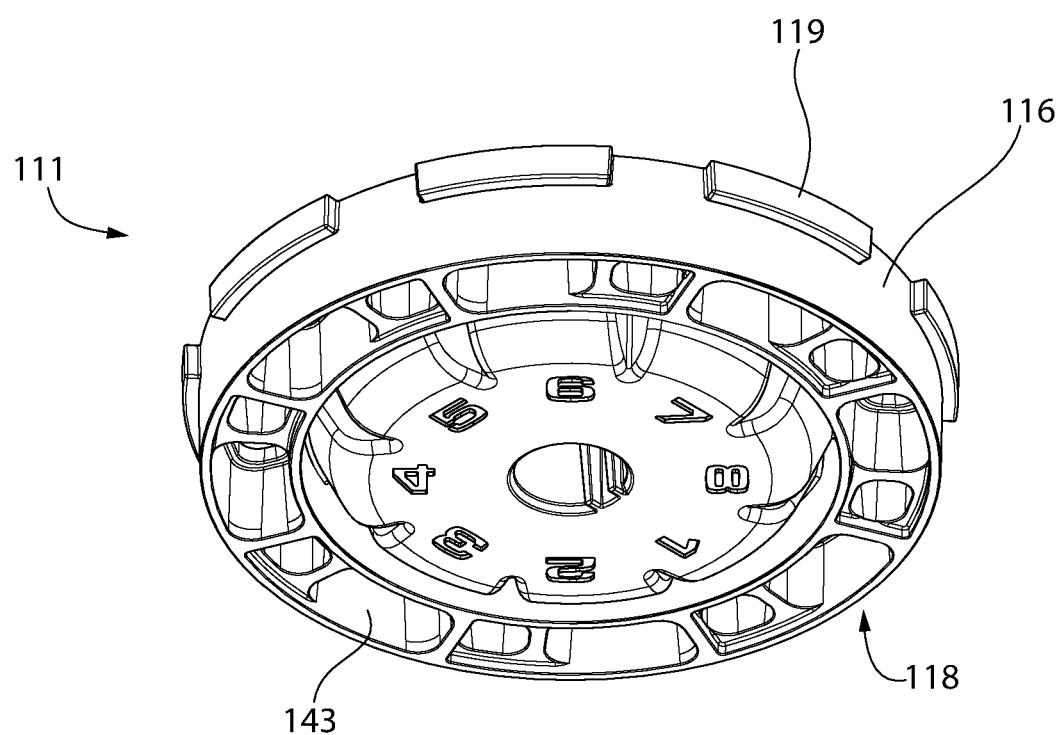
FIG. 10 is a bottom perspective view thereof.
Figure 11:
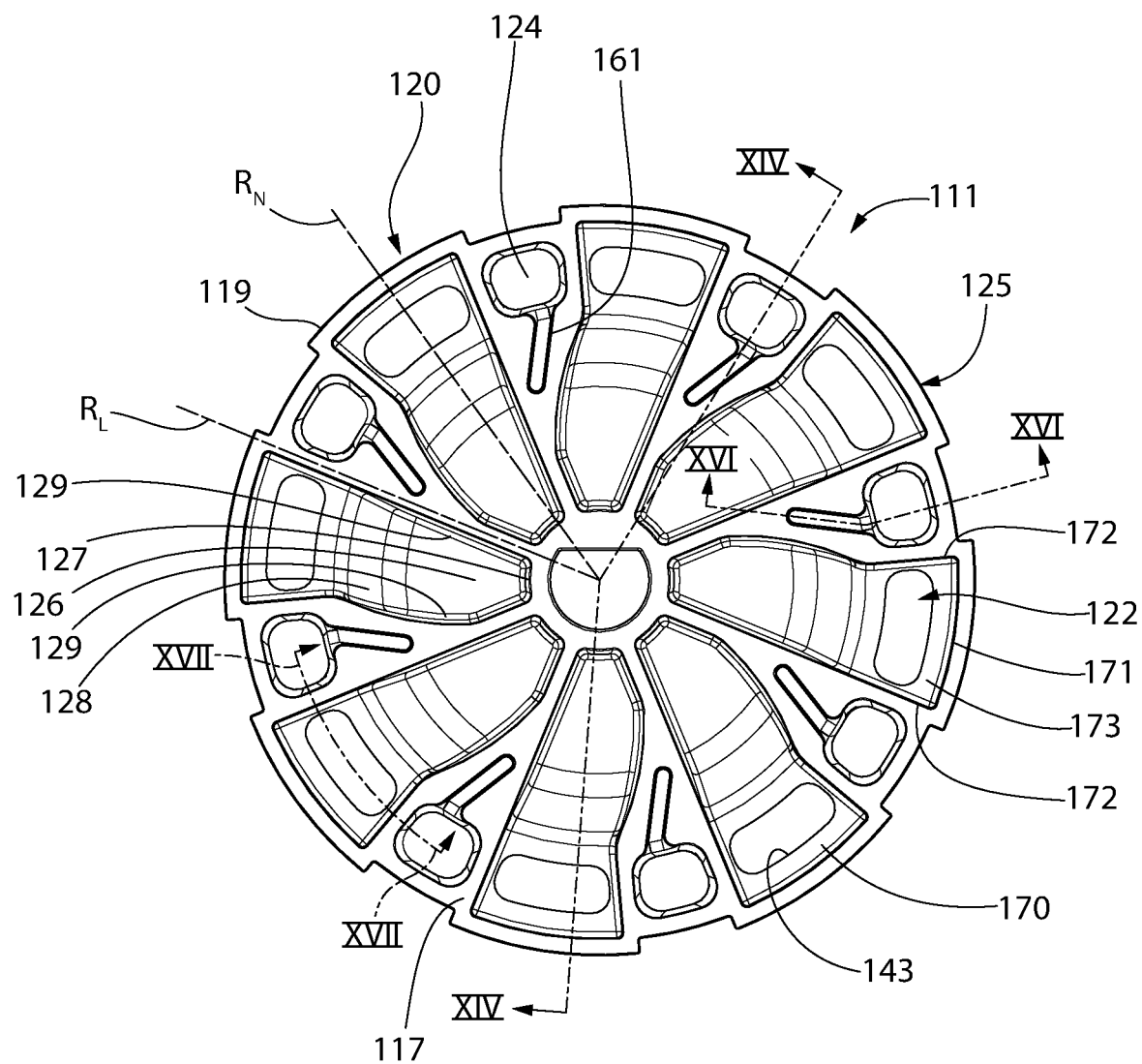
FIG. 11 is a top plan view thereof.
Figure 12:
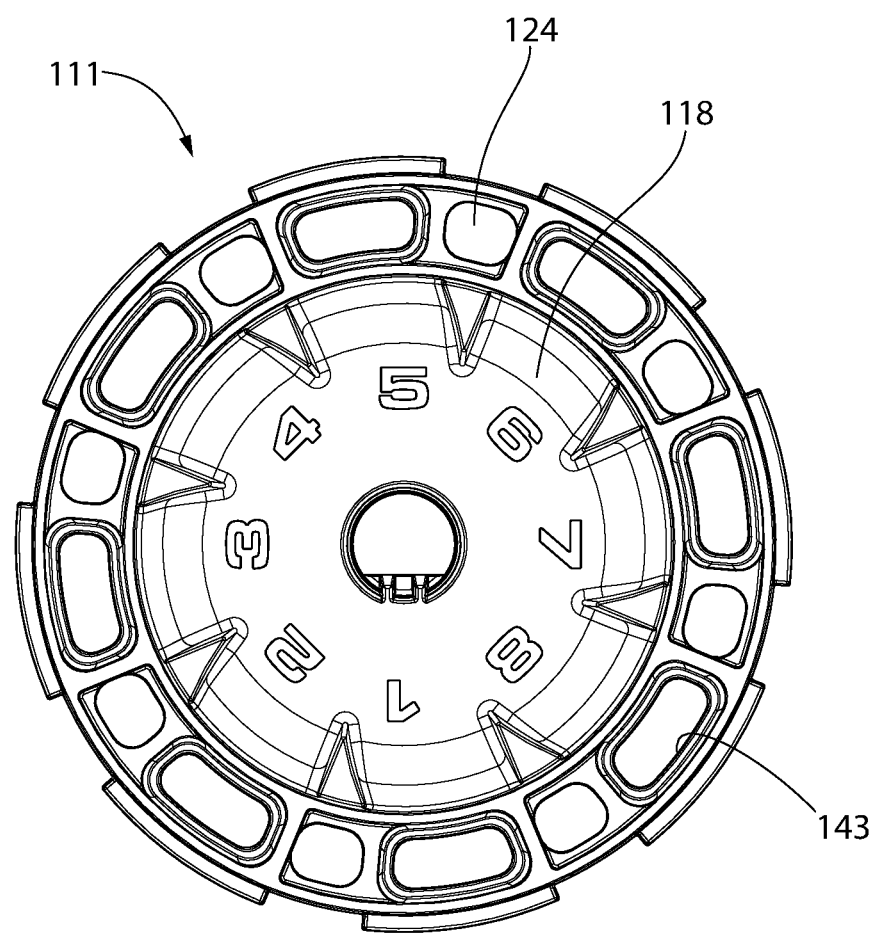
FIG. 12 is a bottom plan view thereof.
Figure 13:
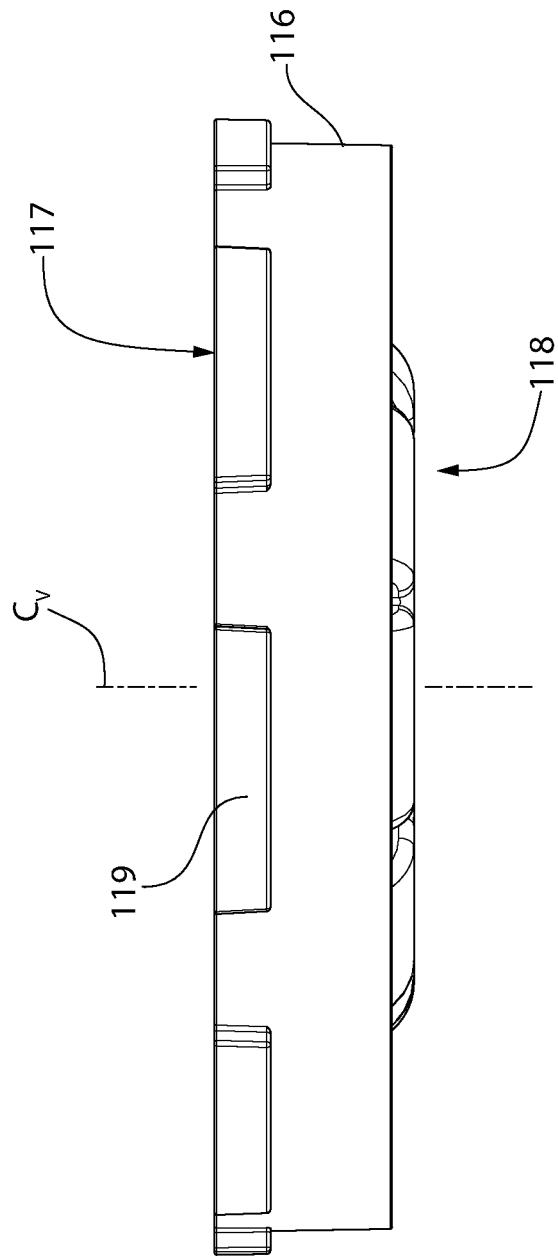
FIG. 13 is a side view thereof.
Figure 14:
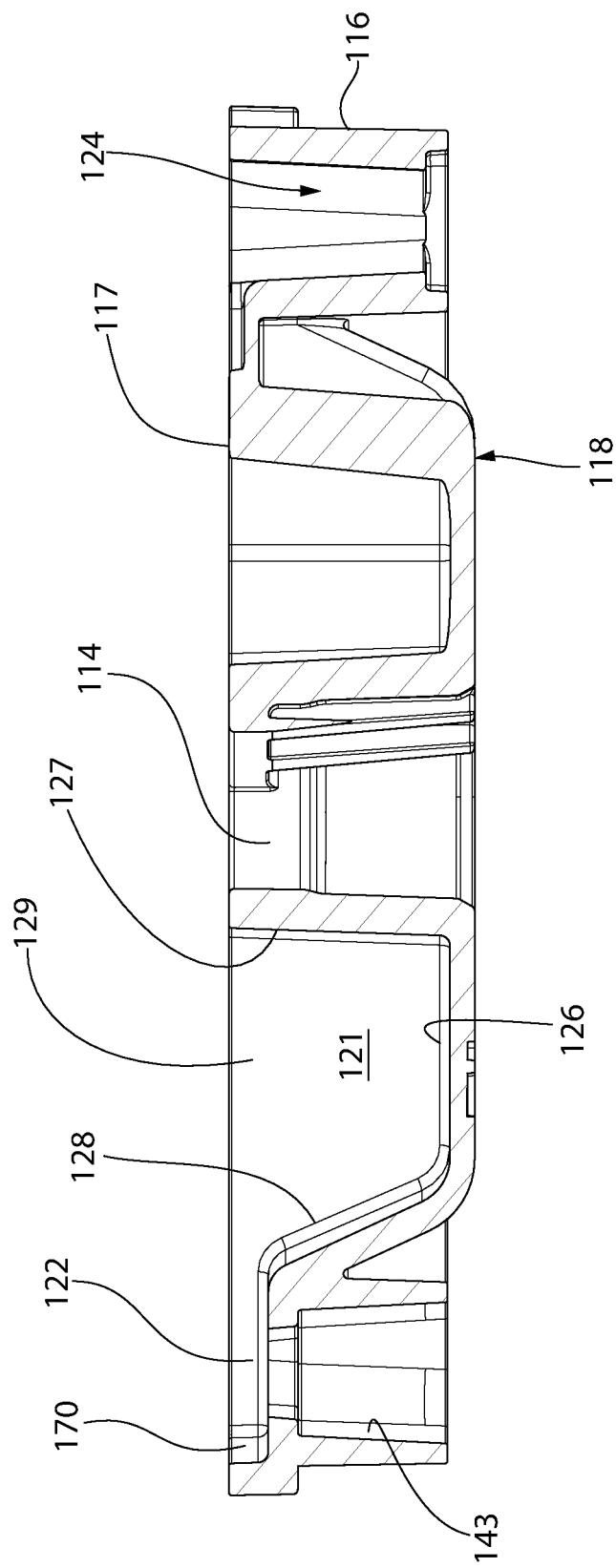
FIG. 14 is transverse cross-sectional view thereof taken from FIG. 11.
Figure 15:
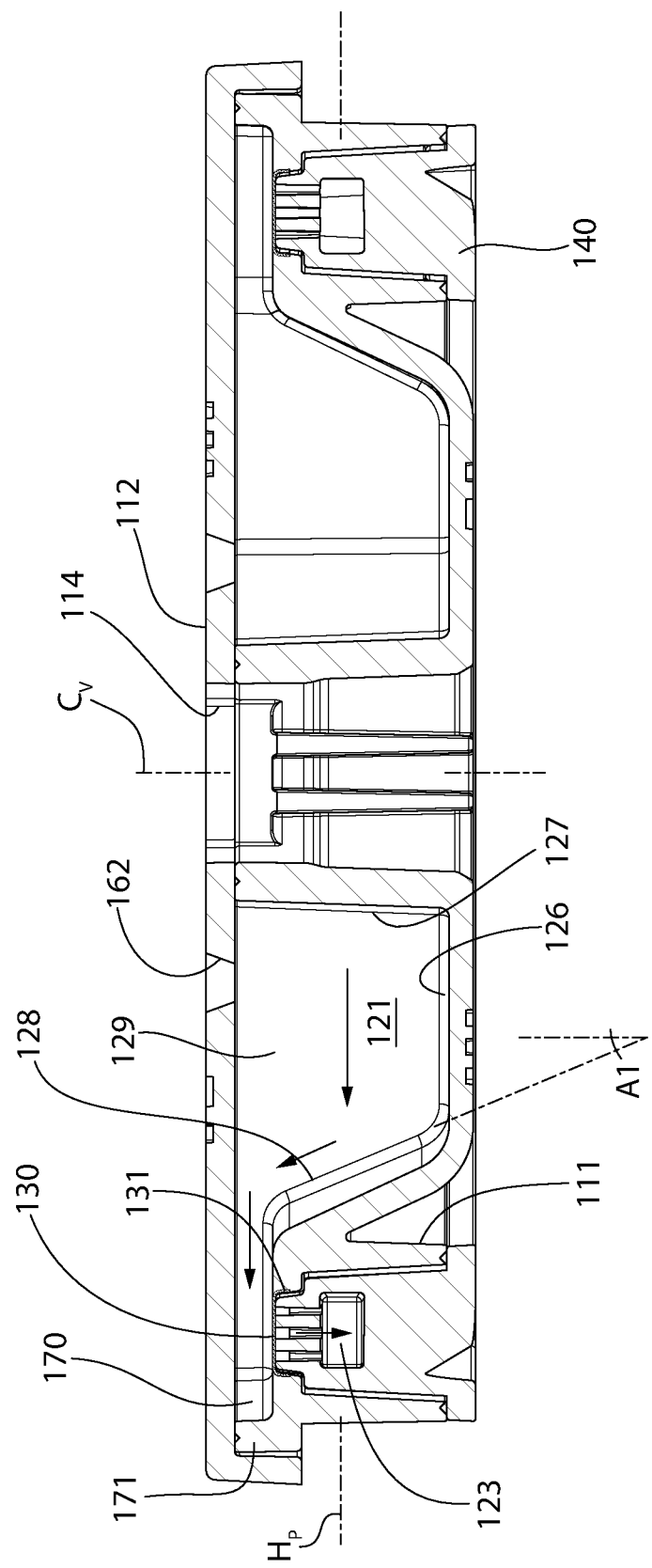
FIG. 15 is transverse cross sectional view of the assembled cartridge of FIG. 1 taken from FIG. 6.

In the non-limiting illustrated construction of the cartridge 110, the extractant mixing chambers 121, slurry filtration chambers 122, reagent mixing chambers 124, and reagent injection conduits 161 may be upwardly open as shown for example in FIGS. 9, 11, and 14. The tops of these chambers and the conduit become closed when top cover 112 is sealingly attached to the main body 111 of the cartridge. The reagent mixing chambers 124 may further be downwardly open until closed by the filter ring 140 (bottom cover 113) when attached to cartridge main body 111 which thereby forms the floors 154 of these chambers. In other possible embodiments, the floors 154 may be integrally molded into the cartridge main body 111 itself instead but preferably formed of a transparent plastic material to allow illumination and colorimetric detection of the supernatant and reagent mixture in the mixing chambers 124.

A process or method for analyzing a soil sample using the rotary soil analysis apparatus 100 including analytical cartridge 110 will now be briefly described with general initial reference to FIGS. 1-17 and 34. The process will be explained with reference to a single sampling train 120 of the cartridge for convenience recognizing that the same procedure applies to the remaining sample trains.

Figure 16:
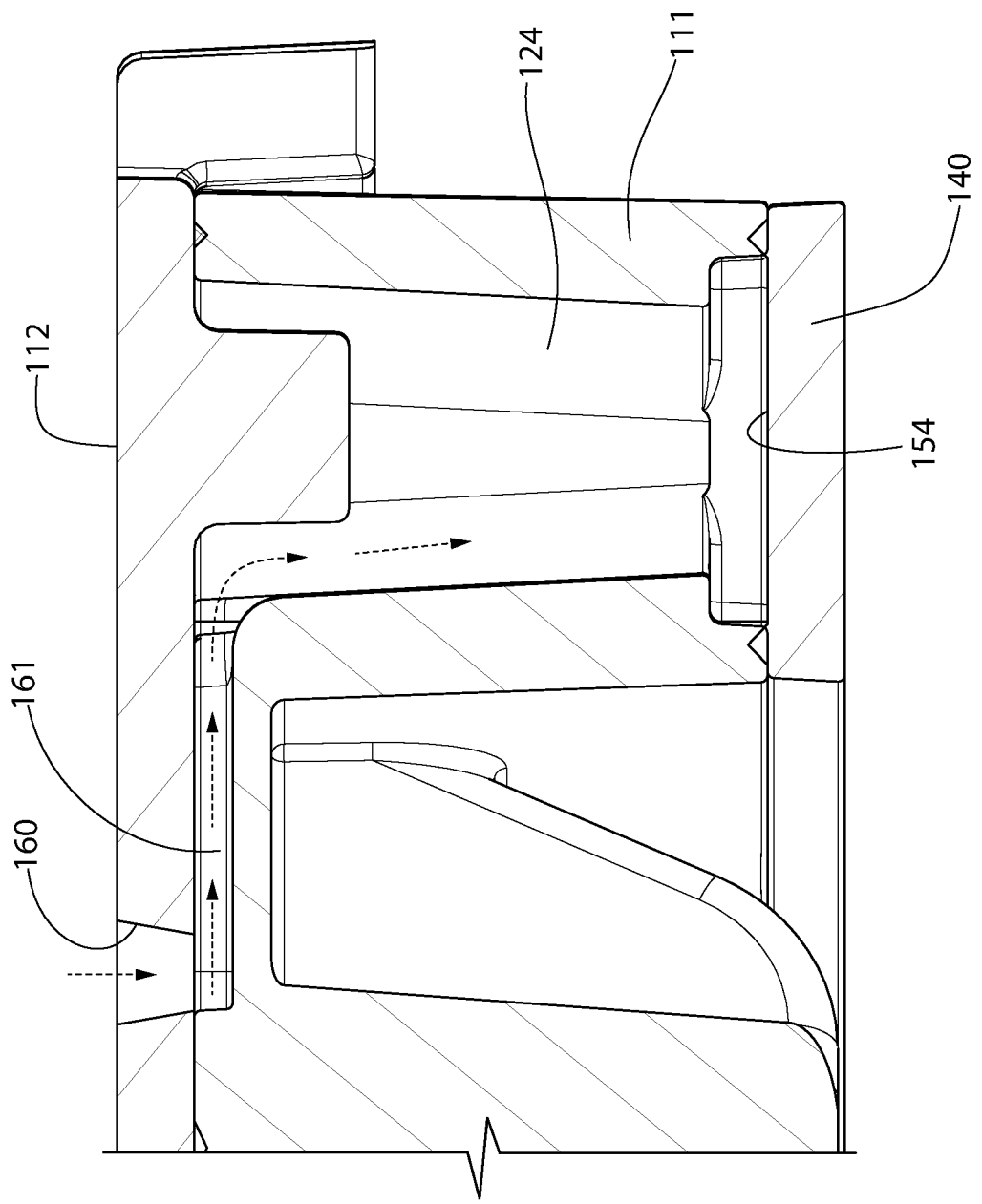
FIG. 16 is a transverse cross sectional view taken from FIG. 11.

First, a color-changing reagent (previously described herein) is added to the reagent mixing chamber via the reagent fill hole 160 in top cover 112 and the injection conduit 161 (see, e.g. FIG. 16 and dashed directional flow arrows). The rotary machine 101 is started which rotates or spins the analytical cartridge 110 in a single rotational direction which drives the reagent fully into the reagent mixing chamber 124 via centrifugal force from the injection conduit. In some embodiments, the reagent may be automatically injected into the cartridge 110 by the rotary machine 101 which may be equipped to store the type of reagents used for processing the sample in all processing chambers. The rotary machine 101 is then stopped.

Before or after depositing the reagent in its mixing chamber 124 in the foregoing manner, a previously collected soil sample is mixed with a sufficient amount of clean water in a sample container to produce a relatively thick slurry. An extractant is then added to the soil slurry which will chemically react with and separate the analyte (substance of interest) to be analyzed from the mixture. Thorough and complete mixing of the extractant with the soil slurry necessary to extract the analyte is performed within the cartridge 110. Examples of typical extractant used in practice are weak acids; however, other types of extractant may of course be used depending on the chemical nature of the analyte to be separated. The soil sample-extractant mixture is now readied for injection into the cartridge 110 and mixing.

The slurry and extractant mixture is then added (e.g. via injection or pouring) to the extractant mixing chamber 121 through the slurry fill hole 162 in the top cover 112. In some embodiments, the slurry-extractant mixture may be automatically injected into the cartridge 110 by the rotary machine 101 which may be equipped to temporarily store the slurry mixture for addition to all extractant mixing chambers 121. Next, the cartridge 110 is rotated with the rotary machine 101 until the extractant is thoroughly mixed with the soil slurry. In one embodiment, a "shaking" type action of the cartridge 110 may be particularly effective. The shaking action may be performed by rapidly oscillating the cartridge 110 in opposing and reverse rotational directions in multiple repetitive cycles each having an angular extent of less than 360 degrees. This effectively shakes and mixes the extractant and slurry mixture thoroughly. In some implementations, the cartridge 110 may preferably be oscillated 90 degrees or less per oscillation in reverse directions. A non-limiting representative example for the total angular range or extent of each oscillation that may be used for cartridge 110 is about and including 1-30 degrees, which is sufficient to mix the extractant with soil slurry in situ within the extractant mixing chamber 121 but avoid flowing the extractant-slurry mixture radially outward in the cartridge for further processing of the soil sample as explained herein. This is achieved by shaking the cartridge 110 as opposed to rotating/centrifugating it in a single direction greater than 360 degrees per rotation.

Next, the cartridge 110 may be rotated and spun in a single direction for multiple revolutions and cycles greater than 360 degrees. The extractant-slurry mixture is driven and flows radially outwards into the slurry filtration chamber 122 via centrifugal force (see, e.g. FIG. 15 and solid directional flow arrows). The soil particles in the slurry mixture are filtered out by the sediment filter 130 and clear supernatant flows downwards into and is collected by the supernatant chamber 123. From there, the supernatant flows from chamber 123 laterally and circumferentially into the reagent mixing chamber 124 with reagent already present as previously described herein (see, e.g. FIG. 17 and solid directional flow arrows). Optionally, another oscillating "shake and mix" sequence may be performed again to ensure thorough mixing of the supernatant and reagent in the reagent mixing chambers 124 if desired for added reassurance.

Once the reagent has completely been mixed and reacted with the supernatant to cause a detectable color change, the rotary machine 101 may be stopped to stop spinning the cartridge 110 for static colorimetric analysis, or the cartridge may continue to spin for dynamic colorimetric analysis. The concentration of the analyte in the reagent mixing chamber 124 may be quantified using the colorimeter integrated into the rotatory machine 101 by shining light form light source 191 (e.g. LEDs) through the chamber and measuring the emitted wavelength of light produced as in a usual colorimetric detection process. The same foregoing process is completed in each of the processing trains 120 of the cartridge 110 in parallel so that multiple analytes may be processed and analyzed simultaneously.

Although in the foregoing example process/method the extractant was first mixed with the soil slurry outside of the analytical cartridge 110, in other embodiments the extractant may instead be added directly to the extractant mixing chamber in liquid form or as a dried/evaporated film.

FIGS. 18-33 depict a second embodiment of a disk-type rotary analytical cartridge 210 in accordance with the present disclosure for use with rotary machine 101. Analytical cartridge 210 includes the same processing chambers as cartridge 110 previously described herein; however, they are arranged in a slightly different manner as explained below. Furthermore, cartridge 210 is distinguishable from cartridge 110 because cartridge-mounted injection plungers are provided for convenience to inject the extractants and reagents to the soil sample being processed. While illustrated herein with a circular shape, cartridge 210 can have any shape that is balanced about centerline axis Cv. In other embodiments, cartridge 210 can be a polygon, a leminiscate, or a rose curve.

Cartridge 210 has a circular disk shape and includes a main body 211 and a top cover 212. A D-shaped central mounting opening 214 is formed at the centerline axis Cv for insertion of the spindle 102 of the rotary machine 101. Opening 214 includes a flat 215 for engaging flat 102a formed on the spindle 102 of the rotary machine 101. In some embodiments, top cover 212 may preferably be transparent or alternatively translucent in other embodiments. This allows the user see the contents of the multiple chambers when processing soil samples and allow light from an external light source 192 of a colorimeter such as LEDs to be shone through reagent mixing chambers 224 (further described herein) for colorimetric detection of analytes and/or chemical properties of the sample supernatant in these chambers. The cartridge main body 211 and top cover 212 may each be formed of a suitable same or different plastic. These components may be injection molded into the configurations and having the features shown. The top cover 212 preferably may be permanently attached to the cartridge main body 211 by any suitable method similar those described with respect to cartridge 110. In one embodiment, ultrasonic welding is used.

Main body 211 of cartridge 210 includes a top surface 217, bottom surface 218, and annular sidewall 216 extending between the top and bottom surfaces. In one embodiment, sidewall 216 may extend parallel to vertical centerline axis CA and perpendicularly to the top and bottom surfaces. Sidewall 216 may have a solid construction in one embodiment.

Each processing train 220 in this embodiment of cartridge 210 generally comprises in fluid communication an extractant mixing chamber 221, an upper slurry filtration chamber 222, a lower supernatant collection chamber 223, and a reagent mixing chamber 224. The listing of the chambers 221-224 is in order of the soil sample slurry and supernatant flow path starting from the initial innermost chamber 221 to the final chamber 224 of each sample processing train 220. In one configuration, the extractant mixing chamber 221, slurry filtration chamber 222, and supernatant collection chamber 223 of each of the sample processing trains 220 may be arranged and radially aligned along a respective radial reference axis Rn already described with respect to cartridge 110. In the present embodiment, the mixing chamber 221 and slurry filtration chamber 222 may share a common recess molded into the main body 211 of the cartridge 210. This advantageously facilitates sealing attaching the top cover 212 to the main body 211 of cartridge 210 and minimizes the number of ultrasonic seal lines 190 required for one processing train 220. The processing chambers of cartridge 210 are each sealed to top cover 212 in a similar manner to cartridge 110 for the same reason in order to fluid isolate the chambers from those in adjacent processing trains 220.

The reagent mixing chambers 224 are angularly and laterally offset from radial reference axis Rn and the slurry filtration chambers 222 which fall on the same imaginary reference circle proximate to the peripheral edge 225 of the main body 211. The extractant mixing chambers 221 and slurry filtration chambers 222 may have a symmetrical shape about radial reference axis Rn, whereas these same chambers in analytical cartridge 110 have an asymmetrical shape about axis Rn. The extractant mixing chambers 221 and reagent mixing chambers 224 may extend for a majority of the full height of the cartridge main body 211. In the present arrangement shown, the slurry filtration chamber 222, supernatant collection chamber 223, and mixing chambers 224 are located radially outwards from the extractant mixing chambers 221. Slurry filtrations chambers 222 each include a sludge collection area 270 arranged radially outwards from the sediment filters 230 similarly to cartridge 110 for collection of soil sludge during sample processing.

Extractant mixing chambers 221 are radially elongated and include a circumferential inner wall 227 nearest central mounting opening 214, an opposing circumferential outer wall 228, a pair of opposing radial walls 229, and a bottom wall 226. The top of mixing chamber 121 is open and closed by the top cover 212 when attached to the main body 211 of the cartridge 210. Radial walls 228 may be non-parallel in one embodiment and gradually diverge moving outwards from the vertical centerline Cv of the cartridge. Arcuately rounded corner portions of each radial wall 228 adjoining the outer wall 228 facilitates smooth flow of the soil slurry to the slurry filtration chamber 222. In one embodiment, inner wall 227 of extractant mixing chamber 221 may have a substantially vertical orientation and the outer wall 228 may be obliquely inclined and angled relative to the vertical centerline axis Cv of the cartridge 210. The outer wall 228 is sloped radially outwards from bottom to top which further facilitates flow from extractant mixing chamber 221 to slurry filtration chamber 222 (best shown in FIG. 32).

The top cover 212 further includes a plurality of soil sample slurry fill holes 262 which open into the extractant mixing chambers 221. This permits a soil slurry without extractant to be injected into each mixing chamber 221. In some embodiments when testing for certain analytes present in or properties of the soil sample, extractant may be mixed with soil slurry before injection into cartridge 210 and a second extractant or another type of chemical may then be injected into the extractant mixing chamber 221 via the plungers 280.

Similarly to cartridge 110, slurry filtering chamber 222 may be vertically positioned on top of the supernatant collection chamber 223 in a stacked manner as shown. A horizontally oriented sediment filter 230 disposed at the bottom of the upper slurry filtering chamber 222 separates that chamber from the lower supernatant collection chamber 223 which are fluidly connected through the filter. Filters 230 may be circumferentially elongated and oblong ovals in one embodiment having a construction similar to sediment filters 130. Filters 230 each include a downwardly extending oblong annular lip 231 which slips over and engage the annular raised lip 273 of cartridge main body 211 (see, e.g. FIG. 32). Filters 230 thus have an inverted U-shape in transverse cross-section in this example embodiment. A plurality of filters 230 are provided and arranged in a circular pattern in the slurry filtration chambers 222 so that each extractant mixing chamber 221 has an associated filter.

Figure 32:
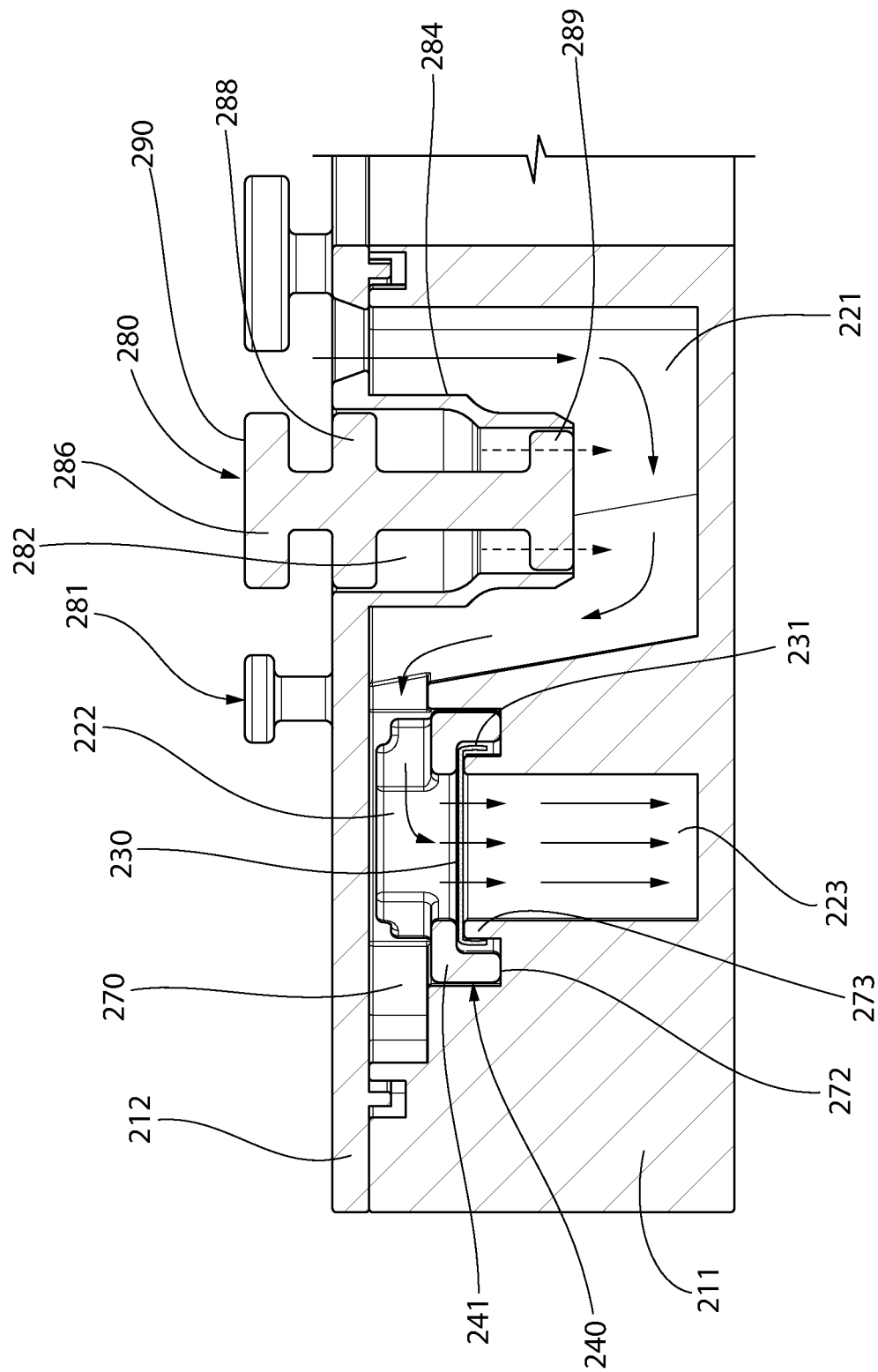
FIG. 32 is transverse cross sectional view of the assembled cartridge of FIG. 18 taken from FIG. 20 from phantom section line XXXII.

In one embodiment with reference to FIGS. 21A-C, 22, and 32, each of the sediment filters 230 may be detachably mounted in main body 211 of cartridge 210 within slurry filtration chamber 222 via a separate annular filter retention ring 240. Retention rings 240 have an oblong oval shape complementary configured to the sediment filters 230. For each slurry filtration chamber 222, the main body 211 of the cartridge defines an annular recessed seating surface 272 with annular raised lip 273 complementary configured to the retention ring 240. Retention rings 240 may include a lower angled L-shaped mounting portion 241 including a vertical leg that engages the seating surface 272 and a horizontal leg that extends over the peripheral portions of the filter 230 and the raised lip 273 of the main body 211, as shown. The retention rings 240 traps the filter 230 in place on the cartridge main body 211. As best shown in FIG. 32, the filters 230 may have an inverted U-shape similar to filters 130 which slips over the raised lip 273 of the main body 211. In one, retention rings 240 may be made of an elastomeric material that frictionally engages the seating surface 272. In other embodiments, the rings 240 may be made of hard plastic.

The reagent mixing chambers 224 may be angularly and laterally offset from the radial reference axes Rn and the supernatant collection chambers 223. Mixing chambers 224 are interspersed between each adjacent processing train 220. The mixing chambers 224 may be located laterally adjacent to and spaced apart from the supernatant collection chambers 223 in one configuration of cartridge main body 211. Pairs of mixing chambers 224 and supernatant collection chambers 223 may be arranged perimetrically around the outer peripheral portion of the cartridge 210 disposed proximate to the annular peripheral edge 225 of the cartridge main body 211 defined by sidewall 216. Chambers 223 and 224 may therefore be located on the same imaginary reference circle of the cartridge. In the present arrangement shown, the slurry filtration chamber 222, supernatant collection chamber 223, and mixing chambers 224 are located radially outwards from the extractant mixing chambers 221. The extractant mixing chambers 221 and reagent mixing chambers 224 may extend for a majority of the full height of the cartridge main body 211.

Figure 33:
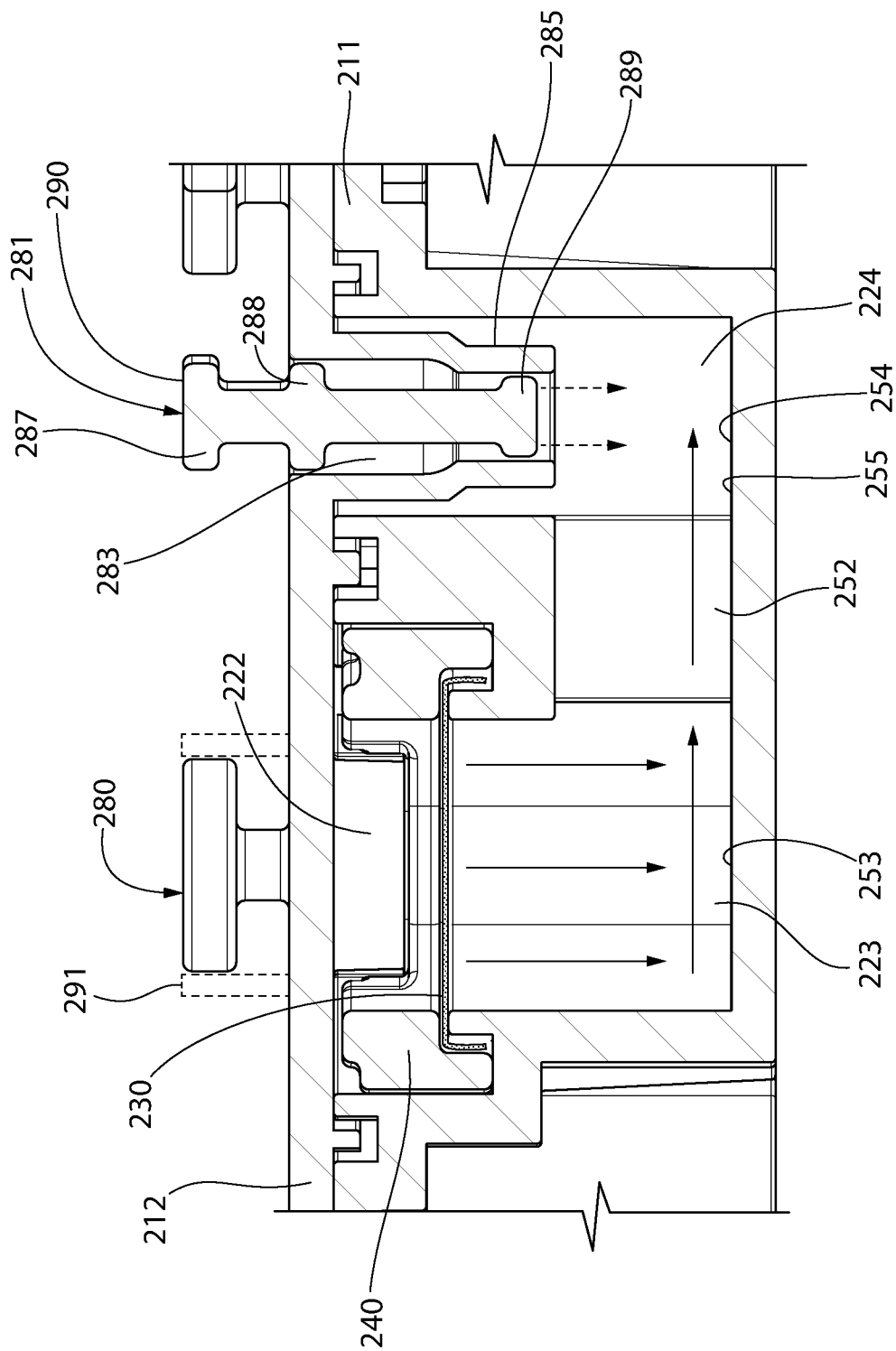
FIG. 33 is a transverse cross sectional view of the assembled cartridge of FIG. 18 taken from FIG. 20 from phantom section line XXXIII.
Figure 34:
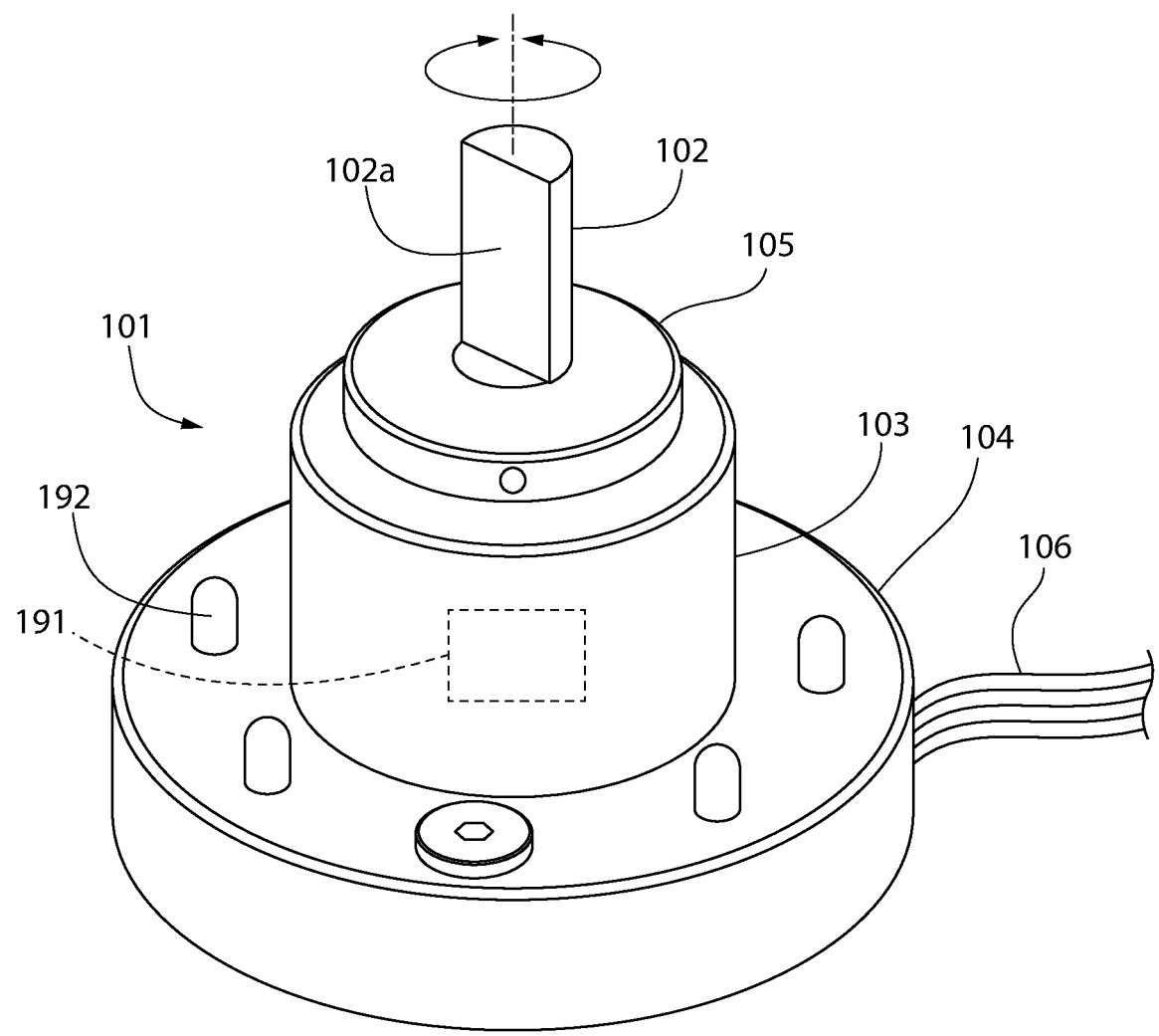
FIG. 34 is a schematic perspective view of a rotary machine with integrated colorimeter operable to rotate or spin the cartridges of FIG. 1 or 18 for processing a soil sample.
Figure 35:
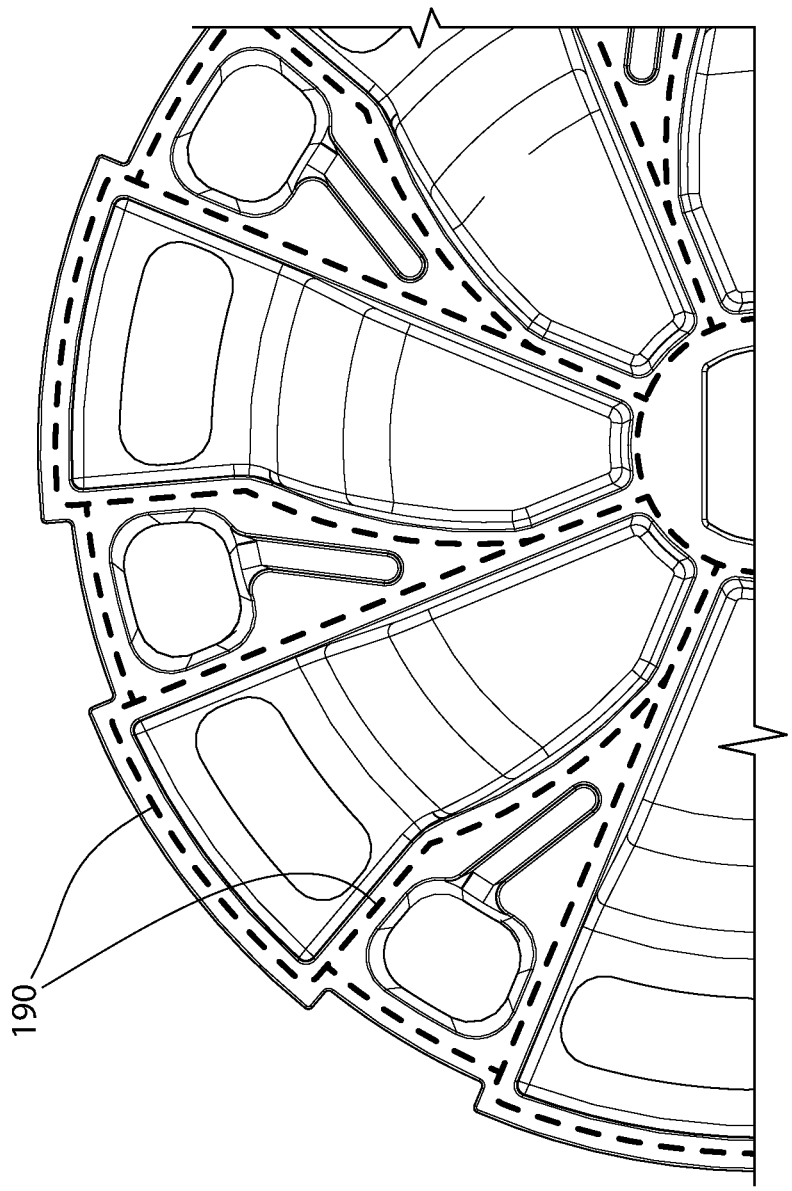
FIG. 35 is a top plan view of the analytical cartridge of FIG. 1 showing ultrasonic welding lines of fusion.

Referring to FIG. 33, the supernatant collection chambers 223 are each fluidly connected to a respective reagent mixing chambers 224 via a laterally and circumferentially extending flow passage 252. Flow passage 252 may be formed proximately to the bottom surface 218 of the cartridge main body 211 and forms a linearly straight supernatant flow path as shown (see solid directional flow arrows). In one embodiment shown, the floor 253 of the supernatant collection chamber 223 may be disposed proximate to the bottom surface 228 of the cartridge main body 211. The floor 253 of collection chamber 223 may be disposed and arranged coplanar with and at the same elevation as the floor 254 of the mixing chamber 224 and floor 255 of the flow passage 252. Supernatant flow from collection chamber 223 to reagent mixing chamber 224 is lateral/circumferential and horizontal. In other embodiments, floor 253 may be higher and not coplanar with floor 254 such that supernatant flows downwards and laterally/circumferentially into reagent mixing chamber 224 via intermediate flow passage 252.

As previously alluded to, analytical cartridge 210 differs from analytical cartridge 110 in that cartridge 210 incorporates plunger assemblies for storage and injection of extractants and reagents into their respective mixing chambers. Referring to FIGS. 32 and 33, cartridge 210 includes pluralities of extractant plunger assemblies 280 and reagent plunger assemblies 281. Each plunger assembly has a volumetric capacity which holds and dispenses the appropriate premeasured dosage of extractant or reagent. One extractant plunger assembly is mounted in each extractant mixing chamber 221 and one reagent plunger assembly 281 is mounted in each reagent mixing chamber 224.

Each plunger assembly 280, 281 includes a cylinder 284, 285 defining an internal cavity 282, 283 having a volumetric capacity and a depressible piston or plunger 286, 287, respectively. Each plunger 286 and 287 is linearly movable and slideable within their respective cylinders 284, 285 for dispensing their contents (i.e. extractant or reagent) into the extractant mixing chambers 221 or reagent mixing chambers 224, respectively. In one embodiment, the cylinders 284, 285 may be integrally molded as unitary structural portions of the plastic top cover 212 as shown. The cylinders 283, 285 are each upwardly and downwardly opened, but closed at the top and bottom when not actuated by annular upper and lower sealing portions 288, 289 integrally formed with the plungers 286, 287. The sealing portions form leak-resistant seals with the interior surface of the cylinders within their internal cavities 282, 283. Plungers 286, 287 may be vertically elongated as shown and formed of an elastomeric material with elastic memory in one embodiment for improved sealing performance. Friction between the elastomeric plungers and cylinders also prevents them from accidentally actuating.

When the plungers 286, 287 are mounted in their cylinders 284, 285 of the cartridge main body 111, an actuator end 290 at the head of each plunger protrudes upwards through openings in the top cover 212. The exposed actuator ends 290 can be depressed downwardly by corresponding automated actuators on the rotary machine 101 or alternatively manually b a user to dispense the contents of the plunger assemblies 280, 281. In some embodiments, an optional annular raised protective rim 291 (example of which is shown in dashed lines in FIG. 33) extending upwards from the top cover 212 may be provided which surrounds each of the actuator ends 290 of the plungers 286, 287. The actuator ends 290 are disposed inside the protective rims 291 which prevent accidental actuation of the plungers.

To inject the reagent or extractant into its respective mixing chamber at the appropriate time, either the rotary machine 101 depresses plungers 280 or 281 downwards at preprogrammed times in the sequence of processing the soil sample, or alternately the user simply depresses the plungers when required. The lower sealing portion 289 emerges from the bottom of its cylinder, thereby breaking the lower seal. The reagent or extractant is injected under positive pressure created by displacement of plunger by the user, and flows downwards into the corresponding mixing chamber (see dashed directional flow arrows). In one embodiment, the extractant plunger assemblies 280 may be larger than the reagent plunger assemblies 281 since the required dosage of extractant may typically be larger than the required reagent dosage needed. However, other size combinations including plunger assemblies of all the same size may be used and is not limiting of the invention.

A process or method for analyzing a soil sample using the rotary soil analysis apparatus 100 including analytical cartridge 210 will now be briefly described with general initial reference to FIGS. 18-34. The process is somewhat and generally similar to that of cartridge 110 with some differences noted below. Similar steps will not be repeated in their entirety but merely referenced in a general manner for the sake of brevity. The method for using cartridge 210 will be explained with reference to a single sampling train 220 of the cartridge for convenience recognizing that the same procedure applies to the remaining sample trains.

First, the reagent is added by actuating reagent plungers 287 to inject the reagent into reagent mixing chamber 224. The cartridge 210 is then spun in a singular direction via rotary machine 101 in the same manner as cartridge 110 previously described herein. Alternatively, this spin step may be omitted since the reagent plunger assemblies 281 are disposed directly in chambers 224.

A soil sample having been collected is mixed with a sufficient amount of clean water in a sample container to produce a relatively thick slurry as previously described with respect to cartridge 110. However, extractant may not be mixed with the slurry outside of the present cartridge. The sample soil slurry mixture is then added (e.g. via injection or pouring) to the extractant mixing chamber 221 through the slurry fill hole 262 in the top cover 212 by the rotary machine 101 or alternatively manually by a user. The extractant plunger 286 is depressed and actuated to inject the extractant directly into mixing chamber 221 (see, e.g. FIG. 32 and dashed directional flow arrows). In an alternate sequence, the extractant may be injected into chamber 221 first followed by adding the soil slurry. In the alternative case where a second extractant or chemical is required to be added via plungers 286 to separate the analyte as previously mentioned, a first extractant may pre-mixed with the soil slurry and the second extractant or chemical is then added via the plunger.

Next, the cartridge 210 is oscillated and shaken with the rotary machine 101 until the extractant is thoroughly mixed with the soil slurry in the same reverse rotational direction partial spins less than 360 degrees in multiple cycles described elsewhere herein. The cartridge 210 is then fully spun (i.e. complete rotations greater than 360 degrees) until the extractant-slurry mixture is driven and flows radially outwards into the slurry filtration chamber 222 (see, e.g. FIG. 32 and solid directional flow arrows). The soil particles in the slurry mixture are filtered out by the sediment filter 230 and clear supernatant flows downwards into and is collected by the supernatant chamber 223. From there, the supernatant flows from chamber 223 laterally/horizontally and circumferentially into the reagent mixing chamber 224 through flow passage 252 (see, e.g. FIG. 33 and solid directional flow arrows). The rotary machine 101 is then stopped, which ceases spinning the cartridge 210. Optionally, another oscillating shake cycle may be repeated to thoroughly mix the supernatant and reagent if necessary.

Once the reagent has completely reacted with the supernatant to cause a detectable color change, the rotary machine 101 may be stopped for static colorimetric analysis or may continue to spin for dynamic colorimetric analysis. The concentration of the analyte in the reagent mixing chamber 124 is quantified using the colorimeter integrated with the rotary machine by shining a light (e.g. LED) through the chamber and measuring the emitted wavelength of light produced as in a usual colorimetric detection process. The same foregoing process is completed in each of the processing trains 120 of the cartridge 110 in parallel so that multiple analytes may be processed and analyzed simultaneously.

It bears noting that the processing chambers of the same type in embodiments of rotary analytical cartridges 110 and 210 (e.g. extractant mixing chambers, slurry filtration chambers, supernatant collection chambers, and reagent mixing chambers) may of the same or different size, shape, and volumetric capacity. These chamber parameters may be varied in each cartridge depending on volume or dosage of extractant or reagent required to extract and detent different types of analytes in the soil sample. In the illustrated embodiments, the processing chambers of each particular type are shown as having the same size, shape, and volumetric capacity.

As illustrated above, analytical cartridges 110 and 210 can be used with colorimetric analysis. Instead of colorimetric analysis, turbidimetric analysis or fluorescence analysis can be used.

As already noted herein, the analysis system and related processes/methods disclosed herein may be used for processing and testing soil, and the analysis system and related processes/methods can also be used for testing other types of fluids, such as vegetation/plants, manure, feed, milk, or other agricultural related parameters of interest. Particularly, embodiments of the analysis system disclosed herein can be used to test for multitude of chemical-related parameters and analytes (e.g. nutrients/chemicals of interest) in other areas beyond soil and plant/vegetation sampling. Some non-limiting examples (including soil and plants) are as follows.

Soil Analysis: Nitrate, Nitrite, Total Nitrogen, Ammonium, Phosphate, Orthophosphate, Polyphosphate, Total Phosphate, Potassium, Magnesium, Calcium, Sodium, Cation Exchange Capacity, pH, Percent Base Saturation of Cations, Sulfur, Zinc, Manganese, Iron, Copper, Boron, Soluble Salts, Organic Matter, Excess Lime, Active Carbon, Aluminum, Amino Sugar Nitrate, Ammoniacal Nitrogen, Chloride, C:N Ratio, Electrical Conductivity, Molybdenum, Texture (Sand, Silt, Clay), Cyst nematode egg counts, Mineralizable Nitrogen, and Soil pore space.

Plants/Vegetation: Nitrogen, Nitrate, Phosphorus, Potassium, Magnesium, Calcium, Sodium, Percent Base Saturation of Cations, Sulfur, Zinc, Manganese, Iron, Copper, Boron, Ammoniacal Nitrogen, Carbon, Chloride, Cobalt, Molybdenum, Selenium, Total Nitrogen, and Live plant parasitic nematode.

Manure: Moisture/Total Solids, Total Nitrogen, Organic Nitrogen, Phosphate, Potash, Sulfur, Calcium, Magnesium, Sodium, Iron, Manganese, Copper, Zinc, pH, Total Carbon, Soluble Salts, C/N Ratio, Ammoniacal Nitrogen, Nitrate Nitrogen, Chloride, Organic Matter, Ash, Conductance, Kjeldahl Nitrogen, *E. coli*, Fecal Coliform, *Salmonella*, Total Kjeldahl Nitrogen, Total Phosphate, Potash, Nitrate Nitrogen, Water Soluble Nitrogen, Water Insoluble Nitrogen, Ammoniacal Nitrogen, Humic Acid, pH, Total Organic Carbon, Bulk Density (packed), Moisture, Sulfur, Calcium, Boron, Cobalt, Copper, Iron, Manganese, Arsenic, Chloride, Lead, Selenium, Cadmium, Chromium, Mercury, Nickel, Sodium, Molybdenum, and Zinc.

Feeds: Alanine, Histidine, Proline, Arginine, Isoleucine, Serine, Aspartic Acid, Leucine, Threonine, Cystine, Lysine, Tryptophan, Glutamic Acid, Methionine, Tyrosine, Glycine, Phenylalanine, Valine (Requires Crude Protein), Arsenic, Lead, Cadmium, Antimony, Mercury Vitamin E (beta-tocopherol), Vitamin E (alpha-tocopherol), Vitamin E (delta-tocopherol), Vitamin E (gamma-tocopherol), Vitamin E (total), Moisture, Crude Protein, Calcium, Phosphorus, ADF, Ash, TDN, Energy (Digestible and Metabolizable), Net Energy (Gain, Lactation, Maintenance), Sulfur, Calcium, Magnesium, Sodium, Manganese, Zinc, Potassium, Phosphorus, Iron, Copper (not applicable to premixes), Saturated Fat, Monounsaturated Fat, Omega 3 Fatty Acids, Polyunsaturated Fat, Trans Fatty Acid, Omega 6 Fatty Acids (Requires Crude or Acid Fat), Glucose, Fructose, Sucrose, Maltose, Lactose, Aflatoxin (B1, B2, G1, G2), DON, Fumonisin, Ochratoxin, T2-Toxin, Zearalenone, Vitamin B2, B3, B5, B6, B7, B9, and B12, Calories, Chloride, Crude fiber, Lignin, Neutral Detergent Fiber, Non Protein Nitrogen, Selenium U.S. Patent, Total Iodine, Total Starch, Vitamin A, Vitamin D3, and Free Fatty Acids.

Forages: Moisture, Crude Protein, Acid Detergent Fiber ADF, NDF, TDN, Net Energy (Gain, Lactation, Maintenance), Relative Feed Value, Nitrate, Sulfur, Copper, Sodium, Magnesium, Potassium, Zinc, Iron, Calcium, Manganese, Sodium, Phosphorus, Chloride, Fiber, Lignin, Molybdenum, Prussic Acid, and Selenium USP.

Milk: Butterfat, True Protein, Somatic Cell Count, Lactose, Other Solids, Total Solids, Added Water, Milk Urea Nitrogen, Acidity, pH, Antibiotic tests, and Micro-organisms.

While the foregoing description and drawings represent some example systems, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof. In addition, numerous variations in the methods/processes described herein may be made. One skilled in the art will further appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims and equivalents thereof, and not limited to the foregoing description or embodiments. Rather, the appended claims should be construed broadly, to include other variants and embodiments of the invention, which may be made by those skilled in the art without departing from the scope and range of equivalents of the invention.

What is claimed is:
1. An analytical cartridge for fluid testing, the cartridge comprising:
 a centerline axis;
 a main body defining a plurality of sample processing trains arranged around the centerline axis, the main body having a mounting opening configured for mounting to a spindle of a rotary machine;

each processing train including an extractant mixing chamber having a slurry fill hole for introducing a slurry and an extractant, and a reagent mixing chamber fluidly coupled to the extractant mixing chamber;

each processing train including a sediment filter configured to deliquify the slurry for producing a supernatant collected in the reagent mixing chamber for analysis;

an annular filter ring separately attached to a bottom of the main body of the cartridge;

wherein the annular filter ring further comprises a plurality of upwardly elongated raised filter housings, each sediment filter being mounted on a respective one of the filter housings.

2. The cartridge according to claim 1, wherein the sediment filters are fluidly interposed between the extractant and reagent mixing chambers.

3. The cartridge according to claim 2, wherein each processing train further includes a set of an upper slurry filtration chamber adjoining and in fluid communication with the extractant mixing chamber and a lower supernatant collection chamber arranged below the upper slurry filtration chamber and fluidly coupled to the reagent mixing chamber.

4. The cartridge according to claim 3, wherein the sediment filter is interposed vertically between the upper slurry filtration chamber and the lower supernatant collection chamber.

5. The cartridge according to claim 3, wherein each upper slurry filtration chamber includes an integrally formed sludge trap arranged radially outwards from the sediment filter to collect sludge removed from the slurry when the cartridge is centrifugated.

6. The cartridge according to claim 3, wherein the lower supernatant collection chamber of each processing train are formed inside the filter housings of the annular filter ring.

7. The cartridge according to claim 6, wherein each sediment filter is detachably mounted on top of a respective one of the filter housings.

8. The cartridge according to claim 3, wherein each extractant mixing chamber is radially elongated and comprises an obliquely inclined outer wall defining an upward sloping surface leading into the upper slurry filtration chamber which is shallower in depth than the extractant mixing chamber to facilitate outward flow of the slurry into the upper slurry filtration chamber when the cartridge is centrifugated.

9. The cartridge according to claim 3, wherein the extractant mixing chamber and upper slurry filtration chamber are each defined by and share a common recess formed in the main body of the cartridge.

10. The cartridge according to claim 9, wherein the common recess gradually diverges moving radially outwards from the centerline axis such that an outer wall of the upper slurry filtration chamber is wider than a circumferential inner wall of the extractant mixing chamber.

11. The cartridge according to claim 3, wherein when the cartridge is rotated by the rotary machine, the slurry flows radially outwards from the extractant mixing chamber into the upper slurry filtration chamber, downwards through the sediment filter into the lower supernatant collection chamber thereby producing the supernatant, and the supernatant flows circumferentially to the reagent mixing chamber.

12. The cartridge according to claim 3, wherein the extractant mixing chamber, upper slurry filtration chamber, and lower supernatant collection chamber of each of the processing trains are radially aligned along a respective radial reference axis of each of the processing trains.

13. The cartridge according to claim 12, wherein each reagent mixing chamber is circumferentially interspersed between each upper slurry filtration collection chamber and each lower supernatant collection chamber, respectively, and laterally offset from the radial reference axes of the processing trains.

14. The cartridge according to claim 1, wherein each extractant mixing chamber is radially elongated and comprises a circumferential inner wall, and opposing obliquely inclined circumferential outer wall, and a pair of radial walls extending between the circumferential inner wall and the circumferential outer wall.

15. The cartridge according to claim 14, wherein the radial walls are non-parallel and gradually diverge relative to each other moving outwards from the centerline axis forming a wedge shaped extractant chamber.

16. The cartridge according to claim 1, further comprising a depressible extractant plunger assembly disposed in the extractant mixing chamber and containing a dosage of extractant, the extractant plunger assembly operable to dispense the dosage of extractant into the extractant mixing chamber by actuating the extractant plunger assembly.

17. The cartridge according to claim 1, further comprising a depressible reagent plunger assembly disposed in the reagent mixing chamber and containing a dosage of a color changing reagent, the reagent plunger assembly operable to dispense the dosage of reagent into the reagent mixing chamber by actuating the reagent plunger assembly.

18. The cartridge according to claim 1, wherein the reagent mixing chamber includes an associated reagent fill hole for introducing reagent into the reagent mixing chamber.

19. The cartridge according to claim 18, wherein each reagent fill hole is fluidly connected to its respective reagent mixing chamber by a reagent injection conduit which extends radially between the reagent mixing chamber and the reagent fill hole.

20. The cartridge according to claim 1, further comprising a top cover enclosing the extractant mixing chamber and the reagent mixing chamber.

21. The cartridge according to claim 20, wherein the top cover is a discrete component sealingly coupled to the main body of the cartridge.

22. The cartridge according to claim 1, wherein each of the processing trains are arranged around the centerline axis in sectors.

23. The cartridge according to claim 1, wherein the main body has a shape that is one of circular, a polygon, a lemniscate, or a rose curve.

\* \* \* \* \*